(12) United States Patent
Elkhail et al.

(10) Patent No.: US 10,834,549 B2
(45) Date of Patent: Nov. 10, 2020

(54) INTERNET OF THINGS FOR HEALTHCARE MONITORING APPLICATIONS BASED ON RFID CLUSTERING SCHEME

(71) Applicant: KING FAHD UNIVERSITY OF PETROLEUM AND MINERALS, Dhahran (SA)

(72) Inventors: Abdulrahman Abu Elkhail, Dhahran (SA); Uthman Baroudi, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 0 days.

(21) Appl. No.: 16/566,412

(22) Filed: Sep. 10, 2019

(65) Prior Publication Data

US 2020/0213823 A1     Jul. 2, 2020

Related U.S. Application Data

(60) Provisional application No. 62/784,969, filed on Dec. 26, 2018.

(51) Int. Cl.
*H04W 4/00*     (2018.01)
*H04W 4/38*     (2018.01)
(Continued)

(52) U.S. Cl.
CPC .............. *H04W 4/38* (2018.02); *G16H 50/30* (2018.01); *H04W 4/80* (2018.02); *H04W 12/0609* (2019.01); *H04W 40/10* (2013.01)

(58) Field of Classification Search
CPC ..... H04W 4/38; H04W 4/80; H04W 12/0609; H04W 40/10; G16H 50/30; G06K 19/0702; G06K 19/0705
See application file for complete search history.

(56) References Cited

U.S. PATENT DOCUMENTS 7,016,306 B2 * 3/2006 Alapuranen ............ H04L 45/00
370/238
7,937,167 B1 * 5/2011 Mesarina .............. H04W 8/186
340/870.11

(Continued)

OTHER PUBLICATIONS

Haiying Shen, et al., "Efficient Data Collection for Large-Scale Mobile Monitoring Applications", IEEE Transactions on Parallel and Distributed Systems, Apr. 18, 2013, pp. 1-11.

(Continued)

*Primary Examiner* — Hai Phan
*Assistant Examiner* — Son M Tang
(74) *Attorney, Agent, or Firm* — Oblon, McClelland, Maier & Neustadt, L.L.P.

(57) ABSTRACT

A system and method for a sensor-based monitoring that includes a computer system, smart nodes, and an RFID reader device. The system collects data to measure health condition of a plurality of people at an event. The computer system determines candidate cluster heads with above average battery level. The smart nodes determine a subset of the candidate cluster heads that are within communication range, retrieve battery level of the determined subset of cluster heads, and select a cluster head having the highest battery level. The selected cluster head announces selection as the selected cluster head, receives requests to join a cluster, reads sensor data of the body sensor in each joined smart sensor as collective sensor data for the cluster, and sends the collective sensor data to the computer system via the RFID reader. Information is collected from smart nodes in an efficient manner for large-scale monitoring systems.

20 Claims, 23 Drawing Sheets

(51) Int. Cl.
*G16H 50/30* (2018.01)
*H04W 4/80* (2018.01)
*H04W 40/10* (2009.01)
*H04W 12/06* (2009.01)

(56) References Cited

U.S. PATENT DOCUMENTS

| | | | | |
|---|---|---|---|---|
| 7,944,899 | B2* | 5/2011 | Nordmark | H04W 40/18 |
| | | | | 370/338 |
| 8,532,008 | B2* | 9/2013 | Das | H04W 52/0219 |
| | | | | 370/311 |
| 9,838,943 | B2* | 12/2017 | Baroudi | H04W 40/08 |
| 9,858,388 | B1* | 1/2018 | Ashoori | G16H 50/30 |
| 10,167,173 | B1* | 1/2019 | Abuelsaad | B66B 25/00 |
| 10,264,511 | B2* | 4/2019 | Baroudi | H04W 40/10 |
| 2005/0222933 | A1* | 10/2005 | Wesby | G06Q 40/00 |
| | | | | 705/36 R |
| 2006/0058155 | A1* | 3/2006 | Kumar | G06F 19/3481 |
| | | | | 482/4 |
| 2008/0132264 | A1* | 6/2008 | Krishnamurthy | H04W 52/46 |
| | | | | 455/522 |
| 2009/0059842 | A1* | 3/2009 | Maltseff | H04W 8/005 |
| | | | | 370/328 |
| 2011/0145631 | A1* | 6/2011 | Shankar | G06F 11/0709 |
| | | | | 714/4.11 |
| 2012/0101912 | A1* | 4/2012 | Sen | G06Q 30/08 |
| | | | | 705/26.3 |
| 2013/0106577 | A1* | 5/2013 | Hinman | G06K 7/10267 |
| | | | | 340/10.1 |
| 2015/0235547 | A1* | 8/2015 | Vardi | G08B 21/0286 |
| | | | | 340/539.12 |
| 2016/0292469 | A1* | 10/2016 | Ianni | G06K 7/10029 |
| 2018/0091875 | A1* | 3/2018 | Bryson | G08B 13/19656 |
| 2018/0295628 | A1* | 10/2018 | Lu | H04W 72/08 |
| 2018/0343602 | A1* | 11/2018 | Baroudi | H04B 7/2606 |

OTHER PUBLICATIONS

P. S. Mano, et al., "Secure Data Transmission in Hybrid Radio Frequency Identification with Wireless Sensor Networks", International Journal of Engineering Research & Technology (IJERT), vol. 3, Issue 07, 2015, pp. 1-5.

* cited by examiner

```
MCU Back-end Server                                              — ☐ ✕

Specifications | Physical | Config | Programming | Attributes

New Project (Python) - main.py

Open | New | Delete | Rename     Reload | Copy | Paste | Undo | Redo | Find | Replace | Zoom: + | — main.py        1   from udp import *
               2   from time import *
               3
               4 ▷ def onUDPReceive(ip, port, data):
               5       info = data.split(",")
               6 ▷     if len(info) == 3:
               7           print(info[0] + "\t" + info[1] + "\t" + info[2])
               8
               9 ▷ def main():
              10       socket - UDPSocket()
              11       socket.onReceive(onUDPReceive)
              12       print(socket.begin(44444))
              13
              14       count - 0
              15 ▷     While True:
              16           count +- 1

Run | Clear Outputs | Help 4 1 0:5:58
10 0 0:6:58
5 0 0:6:7
2 13 0:5:40
7 7 0:6:35
11 5 0:7:5

☐ Top
```

```
● COM10                                                    —  □  ×
┌─────────────────────────────────────────────────────────────┐
│                                                      Send   │
├─────────────────────────────────────────────────────────────┤
│Foreign VALID Tag: 2                                         │
│ID  DAT SEQ_NUM    ID  DAT SEQ_NUM    ID  DAT SEQ_NUM    ID  DAT SEQ_NUM│
│002 067 000 003 , 000 000 000 000 , 000 000 000 000 , 000 000 000 000 ,│
│000 000 000 000 , 000 000 000 000 , 000 000 000 000 , 000 000 000 000 ,│
│000 000 000 000 , 000 000 000 000 , 000 000 000 000 , 000 000 000 000  │
│SIGNATURE:                                                   │
│056 224 047 195 , 209 193 038 098 , 100 000 190 240 , 193 220 136 081  │
│                                                             │
│My Tag:                                                      │
│ID  DAT SEQ_NUM    ID  DAT SEQ_NUM    ID  DAT SEQ_NUM    ID  DAT SEQ_NUM│
│003 071 000 007 , 001 082 000 005 , 000 000 000 000 , 000 000 000 000 ,│
│000 000 000 000 , 000 000 000 000 , 000 000 000 000 , 000 000 000 000 ,│
│000 000 000 000 , 000 000 000 000 , 000 000 000 000 , 000 000 000 000  │
│SIGNATURE:                                                   │
│150 041 073 072 , 061 009 224 003 , 242 202 020 168 , 243 022 014 094  │
│                                                             │
│My Tag:                                                      │
│ID  DAT SEQ_NUM    ID  DAT SEQ_NUM    ID  DAT SEQ_NUM    ID  DAT SEQ_NUM│
│003 071 000 009 , 001 082 000 005 , 002 067 000 003 , 000 000 000 000 ,│
│000 000 000 000 , 000 000 000 000 , 000 000 000 000 , 000 000 000 000 ,│
│000 000 000 000 , 000 000 000 000 , 000 000 000 000 , 000 000 000 000  │
│SIGNATURE:                                                   │
│190 184 013 005 , 048 210 164 251 , 025 037 248 224 , 134 021 147 131  │
└─────────────────────────────────────────────────────────────┘
```

FIG. 28

```
COM10                                                              —   □   ×
┌──────────────────────────────────────────────────────────────┬─────┐
│                                                              │Send │
└──────────────────────────────────────────────────────────────┴─────┘
Foreign NOT VALID Tag: 4
ID  DAT SEQ_NUM     ID  DAT SEQ_NUM     ID  DAT SEQ_NUM     ID  DAT SEQ_NUM
004 000 000 000 , 000 000 000 000 , 000 000 000 000 , 000 000 000 000 ,
000 000 000 000 , 000 000 000 000 , 000 000 000 000 , 000 000 000 000 ,
000 000 000 000 , 000 000 000 000 , 000 000 000 000 , 000 000 000 000
SIGNATURE:
000 000 000 000 , 000 000 000 000 , 000 000 000 000 , 000 000 000 000

My Tag:
ID  DAT SEQ_NUM     ID  DAT SEQ_NUM     ID  DAT SEQ_NUM     ID  DAT SEQ_NUM
003 071 000 010 , 001 082 000 005 , 002 067 000 003 , 000 000 000 000 ,
000 000 000 000 , 000 000 000 000 , 000 000 000 000 , 000 000 000 000 ,
000 000 000 000 , 000 000 000 000 , 000 000 000 000 , 000 000 000 000
SIGNATURE:
192 217 070 054 , 219 101 120 035 , 090 005 027 154 , 207 144 201 073

My Tag:
ID  DAT SEQ_NUM     ID  DAT SEQ_NUM     ID  DAT SEQ_NUM     ID  DAT SEQ_NUM
003 071 000 012 , 001 082 000 005 , 002 067 000 003 , 000 000 000 000 ,
000 000 000 000 , 000 000 000 000 , 000 000 000 000 , 000 000 000 000 ,
000 000 000 000 , 000 000 000 000 , 000 000 000 000 , 000 000 000 000
SIGNATURE:
132 223 213 129 , 155 194 069 155 , 165 252 082 062 , 206 167 048 251
```

INTERNET OF THINGS FOR HEALTHCARE MONITORING APPLICATIONS BASED ON RFID CLUSTERING SCHEME

CROSS-REFERENCE TO RELATED APPLICATIONS

This application claims the benefit of priority to provisional application No. 62/784,969 filed Dec. 26, 2018, the entire contents of which are incorporated herein by reference.

STATEMENT OF ACKNOWLEDGEMENT

The authors would like to acknowledge the support provided by the Deanship of Scientific Research (DSR) at King Fand University of Petroleum and Minerals (KAUST-KFUPM) through research grant RG1424-1.

BACKGROUND OF THE INVENTION

Field of the Invention

The present disclosure is directed to a healthcare monitoring system in which health data is collected using a hybrid radio-frequency identification (RFID) and wireless sensor network (WSN) system based on a clustering scheme.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

The development of Wireless Sensor Networks (WSNs) has contributed to enhancement of the Internet of Things (IoT) technology. A Wireless Sensor Network refers to a network of spatially dispersed and dedicated sensors for monitoring and recording physical conditions of the environment and organizing the collected data at a central location. The topology of WSNs may range from a star network to a multi-hop wireless mesh network. A wireless mesh network uses a mesh topology of many-to-many interconnections among devices or nodes. However, a wireless mesh network typically requires low mobility among the devices or nodes so that overhead related to route updates is minimized. Multi-hop routing is a type of communication in radio networks in which network coverage area is larger than radio range of its nodes. To reach distant nodes, a node can use intermediate nodes as relays.

The WSN is a network of nodes, where each node is connected to one or more sensors. A typical sensor node has several parts, including a radio transceiver with an internal antenna or connection to an external antenna, a microcontroller, an electronic circuit for interfacing with the one or more sensors and a power source, such as a battery.

In a case of healthcare monitoring, sensor nodes include medical devices that may be implanted, wearable, and environment-embedded. Implantable medical devices are those that are inserted inside the human body. Wearable medical devices are placed on the body surface of a human or at close proximity of the human. The medical devices may be used for body position measurement, location of persons, monitoring of patients health, such as temperature and blood pressure.

Radio-Frequency Identification (RFID) uses electromagnetic fields to identify and track tags attached to objects. The tags electronically store information. RFID tags typically contain an integrated circuit that stores and processes information and that modulates and demodulates radio-frequency signals, a coiled antenna for collecting power from an incident reader signal and for receiving and transmitting the signal. The tag information may be stored in a non-volatile memory. RFID tags are typically used to track and manage inventory, assets, people, animals, or other objects. Subsequently, a common type of data stored in a tag is an Electronic Product Code.

The information stored in a tag may be read by an RFID reader. The RFID reader, via a two-way radio transmitter-receiver, sends a signal to the tag and reads its response. The REID tag receives the message and then responds with the tag's identification and other information. The RFID reader may be a passive reader, an active reader for a passive tag, or an active reader for an active tag. The passive reader only receives radio signals from active tags (battery operated). The active reader for an active tag can wake active tags with an interrogator signal. RFID readers may be fixed to create a specific interrogation zone which can be tightly controlled, or may be mobile.

The combination of Radio-Frequency Identification (RFID), Wireless Sensor Networks (WSN) and Internet of Things (IoT) technologies together provide an efficient smart environment that is applicable to a wide variety of applications such as tracking systems, medical treatment, environmental monitoring, Intelligent Transportation System (ITS), public health, smart grid, and many other areas. See Kai Zhao and Lina Ge. "A survey on the internet of things security." Computational Intelligence and Security (CIS), 2013 9th International Conference on. IEEE, 2013, incorporated herein by reference in its entirety.

RFID has many advantages. Firstly, it is very simple and easy to install. Also it is very efficient in terms of cost and power consumption and can be combined with sensors. See H. Shen, Z. Li, L. Yu and C. Qiu, "Efficient Data Collection for Large-Scale Mobile Monitoring Applications," in IEEE Transactions on Parallel and Distributed Systems, vol. 25, no. 6, pp. 1424-1436, June 2014, incorporated herein by reference in its entirety. RFID is the process and physical infrastructure by which a unique identifier, within a pre-defined protocol definition, is transferred from a device to a reader via radio frequency waves.

RFID tags can be passive, active or battery-assisted-passive (BAP). The active and BAP tags both contain batteries that allow them to communicate in a wider range that can go up to 1 km for enterprise uses and over 2 km in military applications. Unlike battery powered tags, passive tags use the RF signal provided by the RFID reader to generate power and transmit/receive data. This property of passive tags allows it to be very cheap and gives it a long life time, but it also introduces a bigger issue which is the dependence on orientation angle.

FIG. 1 is a schematic of an architecture of a passive RFID tag that is powered by the RFID reader's RF signal using a coiled antenna. The passive RFID tag 100 includes an RFID Reader 110 and an RFID Transponder 120. The RFID Reader 110 includes a transceiver 103 that receives a data signal 101 and generates a modulated RF field, and outputs a transceiver field signal 105. The RFID transponder 120 modulates the transceiver field 105 with tag data and stores the data in the passive tag 107. Based on the architecture of the passive tag, the positioning of the coiled antenna that powers the tag is crucial and can cause it to work in a limited range of angles. See Klaus Finkenzeller, RFID Handbook: Fundamentals & Applications in contactless Smart cards, Radio frequency Identification & near field communication, John Wiley & Sons, third edition 2010, incorporated herein by reference in its entirety. RFID can be attached to the items to be recognized, enhancing the efficiency of monitoring and managing objects. See Vaerenbergh S M, Legros C P. Influence of thermal boundary conditions on the double-diffusive process in a binary mixture. Int. J. Thermal & Environmental Engineering 2010; 1:109-129; Haik, Y: Engineering Design Process. Pacific Grove: Brooks/Cole, 2003; Toukourou N M, Gakwaya B, Yazdani J J. An object-oriented finite element implementation of large deformation frictional contact problems and applications. Proceedings of the 1st MIT conference on CFSM. Cambridge, Mass., 2001; and Peky G K. X-Analysis Integration (XAI) Technology. Virginia Tech Report EL002-2000A, March 2010, each incorporated herein by reference in their entirety.

Having real-time data collection and management is very important especially in a healthcare related system as the United Nations International Children's Emergency Fund (UNICEF) and the World Health Organization (WHO) reported in 2016 that more than 295 thousand women die every year from causes related to pregnancy and childbirth. See Hofmeyr, G. J Qureshi, Z. (2016). Preventing deaths due to hemorrhage. Best Practice & Research Clinical Obstetrics & Gynaecology, 36, 68-82, incorporated herein by reference in its entirety. This is due to the unavailability of timely medical treatments. Moreover, the report stated that the main reasons of cancer related deaths are due to the late detection of the abnormal cellular growth at the last stage. Many lives can be saved by utilizing IoT smart nodes that can detect cancer in the primary stage. WSNs have mainly been utilized for observing physical or ecological conditions, gathering natural information, for example, heartbeat, muscle activation, etc.

Much research has focused on health care monitoring by using either RFID or WSN as the short-range radio interfaces. However, very little of this research relates to solutions that are suitable for healthcare monitoring applications for a large-scale system that addresses a hugely crowded area with high mobility.

In particular, Sun Microsystems in collaboration with the University of Freibourg have proposed a web-based application called (RFID-Locator) to improve the quality of hospital services. See P. Fuhrer and D. Guinard, "Building a smart hospital using RFID technologies," in Proc. 1st Eur. Conf. eHealth (ECEH'06), October 2006, vol. P-91, pp. 131-142, incorporated herein by reference in its entirety. RFID-Locator tracks the patients and goods in the hospital as one approach to building a smart hospital. All patients in the hospital are given an RFID based on a wristband resembling a watch with a passive RFID tag in it. All of the patients' histories and treatment records are stored in a secure centralized database. Doctors have RFID-enabled personal data assistant (PDA) devices to read patient data obtained from or associated with the patient's RFID tag. The results are promising but much work is needed in the security and encryption of the collected data and in the energy efficiency area.

Dsouza et al. have proposed a wireless localization network to follow the location of patients in indoor environments as well as to monitor their activity status i.e. walking, running, etc. See M. D'Souza, T. Wark, and M. Ros, "Wireless localization network for patient tracking," in Proc. Int. Conf. Intell. Sensors Sensor Netw. Inf. Process., December 2008, pp. 79-84, incorporated herein by reference in its entirety. Dsouza et al. deploy static nodes at different locations of the hospital that interact with the patients' mobile units to determine the patients' locations in the building. Each patient carries a small mobile node that includes a small sized Fleck Nano wireless sensor and a three-axis accelerometer sensor in order to monitor their physical status. However, using all patients' smartphone GPS processes and Wi-Fi activation is not an energy efficient solution because it requires high power.

Chandra-Saharan et al. have proposed a location-aware WSN to track people in a disaster site using a ranging algorithm. See A. K. Chandra-Sekaran, P. Dheenathayalan, P. Weisser, C. Kunze, and W. Stork, "Empirical analysis and ranging using environment and mobility adaptive RSSI filter for patient localization during disaster management," in Proc. Int. Conf. Netw. Services (ICNS'09), 2009, pp. 276-281, incorporated herein by reference in its entirety. The ranging algorithm is based on received signal strength indicator (RSSI) environment and mobility adaptive (REMA) filter. The REMA filter can estimate the real-time localization of people at the disaster site using RSSI and Global Positioning System (GPS). However, using GPS for many people is not an energy efficient solution.

Xiaoguang and Wei have proposed an adaptive communication framework to build a smart hospital warehouse based on integration between RFID and WSN. See Z. Xiaoguang and L. Wei, "The research of network architecture in warehouse management system based on RFID and WSN integration," in Proc. IEEE Int. Conf. Autom. Logist., September 2008, pp. 2556-2560, incorporated herein by reference in its entirety. The main components of the proposed solution include RFID tags, sensors, reader and center data platform. The authors evaluate their solution based on three network architectures which are a heterogeneous network architecture, a smart sensor tag network architecture, and a smart reader network architecture. Their evaluation revealed many challenging issues. For example, the reliability of the sensors and the true dependence of the reader's node are issues that need to be addressed.

Charalampos and Ilias have developed a Cloud-based system that consists of sensors, sensors getaway, and communication APIs provided by the Cloud platform. The system manages and collects the data (bio signals, motion data and contextual data), and forwards this data to the cloud using wireless technology and then to an external application which provides the necessary real-time data monitoring and management. See C. Doukas and I. Maglogiannis, "Bringing IoT and Cloud Computing towards Pervasive Healthcare," 2012 Sixth International Conference on Innovative Mobile and Internet Services in Ubiquitous Computing, Palermo, 2012, pp. 922-926, incorporated herein by reference in its entirety. The results are promising but much work is still needed in the areas of security and encryption of the collected data and in energy efficiency.

The authors in Shen et al. propose a hybrid RFID and WSN system (HRW). Their system is mainly built using smart nodes and RFID readers to collect data from the smart nodes and send the collected data to the last component back-end server for data processing. The smart nodes, also referred to as Hybrid Smart Nodes, combine the function of RFID tags, and reduced function of wireless sensors and RFID readers. The smart nodes actively transmit data to readers in a multi-hop manner. Using proactive data transmission, smart nodes read tag data between each other, such that the RFID reader can receive the information of a group of tags by reading only one first-encountered node. Also, a smart node can read data from the RFID tag of another node even if it is in sleep mode.

The smart nodes in Shen et al. include a reduced-function sensor, an RFID tag and a reduced-function RFID reader (RFRR). The sensor is a reduced-function sensor that does not have a transmission function. Instead, the sensor collects the environment data and the sensed data from hosts. The RFID tag, as with normal RFID tags, serves as traditional packet memory buffer for information storage. RFID information such as identity and properties is configured into the RFID tag during production. The RFRR can be a simple ultra-high frequency reader module and is used for data transmission between smart nodes.

The smart node uses RFRR to read other smart nodes' tags and write the information to its own tag. After a smart node collects sensed data, it appends the sensed data with a timestamp and stores the data in its tag through the RFRR. Once two nodes move into the transmission range of each other, the RFRR in one smart node reads the information stored in the other node's tag. Based on the host ID and timestamp, the reading smart node checks if it has stored the information previously. If not, the RFRR of the reading smart node then stores the acquired information into the local tag. In this manner, smart nodes may replicate data of other smart nodes.

Any one of the smart nodes that moves into transmission range of the RFID reader can transmit the information to the reader. In particular, when a node enters the reading range of an RFID reader, the RFID reader reads the information in the node's tag. If several nodes enter the range of the RFID reader at the same time, the RFID reader gives the first entering tag the highest priority to access the communication channel. An RFID reader can erase the information in the tag of the smart node after obtaining it. In order to reduce unnecessary message transmission because many nodes still hold replicas of the information, a tag clean-up algorithm is used to delete the delivered messages in the system.

Shen et al. further describes enhanced data transmission algorithms to avoid problems related to data replication and the need to erase duplicate data that has been reported to RFID readers. Two enhanced algorithms include a cluster-member based algorithm and a cluster-head algorithm. In the cluster-member based algorithm, the RFID reader receives all information of nodes in a virtual cluster by reading aggregated tag information from one cluster member. In the cluster-head based algorithm, cluster members replicate their tag data to the cluster head.

According to Shen et al., to form the clusters in the cluster-member based algorithm, nodes report their encountering frequency to the server through the RFID readers. The server forms nodes with high encountering frequency into a cluster and notifies the cluster nodes through the RFID readers. The cluster head for a cluster can be selected in a number of ways depending on the application requirement. For example, in a health monitoring application where real-time data collection is required, the nodes with the most contact frequency with cluster members and RFID readers may be the cluster heads. In the supply chain where nodes are always close to each other, the nodes with the highest energy may be the cluster heads.

In a similar manner, Mano et al., "Secure data transmission in hybrid radio frequency identification with wireless sensor networks," International Journal of Engineering Research and Technology, Volume 3, Issue 07, 2015, describes a network in which RFID and WSN are used to monitor and sense the environmental conditions then send the data. Like Shen et al., the smart nodes include a reduced function sensor, an RFID tag, and reduced-function RFID reader. Nodes can exchange and replicate node details with each other. The data transmissions in the RFID readers use the multi-hop transmission mode of the wireless sensor network. With multi-hop transmission, each RFID reader can receive data information from other outside readers within its range. The system contains two components including an event manager and RFID information server. The event manager collects the information and stores the detailed information. The RFID information server stores the information in the backend server.

Similar to Doukas et al., authors in Amendola et al. focused on healthcare area and provided a survey shows the current study on RFID sensing from the viewpoint of IoT for individual healthcare also prove that (RFID) technology is now established to be part of the IoT. See S. Amendola, R. Lodato, S. Manzari, C. Occhiuzzi and G. Marrocco, "RFID Technology for IoT-Based Personal Healthcare in Smart Spaces," in IEEE Internet of Things Journal, vol. 1, no. 2, pp. 144-152, April 2014, incorporated herein by reference in its entirety. On the other hand, the paper reveals many challenging issues, for example, the reliability of the sensors and the true dependence of the reader's node. There are even more advanced solutions provided in Yang et al. the authors proposed an iHome approach which consists of three key blocks, the iMedBox, the iMedPack, and the Bio-Patch. See G. Yang et al., "A Health-IoT Platform Based on the Integration of Intelligent Packaging, Unobtrusive Bio-Sensor, and Intelligent Medicine Box," in IEEE Transactions on Industrial Informatics, vol. 10, no. 4, pp. 2180-2191, November 2014, incorporated herein by reference in its entirety. RFID tags are used to enable communication capabilities to the iMedPack block also flexible and wearable biomedical sensor devices are used to collect data (Bio-Patch). The results are promising but the study didn't consider sensor devices for monitoring purposes.

Another Smart Healthcare System is proposed in Catarinucci et al. to monitor and track patients, personnel, and biomedical devices automatically using deferent technologies including RFID, WSN, and smart mobile. See L. Catarinucci et al., "An IoT-Aware Architecture for Smart Healthcare Systems," in IEEE Internet of Things Journal, vol. 2, no. 6, pp. 515-526, December 2015, incorporated herein by reference in its entirety. In order to allow these different technologies to interoperate, complex network communications relying on a CoAP, 6LoWPAN, and REST paradigms have been implemented as two use cases. The results provided good performance not only to operate within hospitals but to provide power effective remote patient monitoring. The results are promising but their approach needs more information concerning an infrastructure that combines wired and wireless sensor network.

Gope and Hwang have proposed a secure IOT healthcare application using a body sensor network (BSN) to monitor patient's health using a collection of tiny-powered and lightweight wireless sensor nodes. See Gope, P., & Hwang, T. (2016). BSN-Care: A secure IoT-based modern healthcare system using body sensor network. IEEE Sensors Journal, 16(5), 1368-1376, incorporated herein by reference in its entirety. In addition, the system can efficiently protect patient's privacy by utilizing a lightweight anonymous authentication protocol, and the authenticated encryption scheme offset codebook (OCB). The lightweight anonymous authentication protocol can achieve mutual authentication, preserve anonymity, and reduce computation overhead between nodes. The OCB block cipher encryption scheme is well-suited for secure and expeditious data communication as well as efficient energy consumption. The results are promising but their approach needs more detailed information concerning infrastructure.

It is one object of the present disclosure to describe a method, system and computer program product based on Internet of Things (IoT) that integrates RFID with wireless sensor networks based on a clustering scheme to monitor and collect data in an efficient way in a large populous area. Other objectives include a clustering scheme that minimizes the total distance between cluster heads and cluster members and that minimizes the number of clusters. In some aspects, the technique reduces the communication burden on the reader by reading only the cluster head node within its range.

SUMMARY

In an exemplary embodiment, a sensor-based monitoring system and method of collecting data to measure health condition of a plurality of people at an event is disclosed. The sensor-based monitoring system includes a computer system; a plurality of smart nodes for the plurality of people, each smart node including a radio frequency identification (RFID) tag, a wireless sensor network communication device, and at least one body sensor; and at least one RFID reader device. The computer system includes circuitry configured to determine candidate cluster heads as smart nodes with above average battery level. Each of the plurality of smart nodes are configured to determine a subset of the candidate cluster heads that are within communication range, retrieve a battery level of the determined subset of cluster heads, select a cluster head having the highest battery level. The selected cluster head is configured to send a message to announce selection as the selected cluster head, receive messages, from the plurality of smart nodes that are within communication range, requesting to join a cluster, read sensor data of the body sensor in each joined smart sensor as collective sensor data for the cluster, and send the collective sensor data to the computer system via the at least one RFID reader. The circuitry of the computer system is further configured to measure the health conditions of the plurality of people at the event based on the sent collective sensor data.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 20 illustrates a sample of the collected data at the back-end server;

Figure 21:
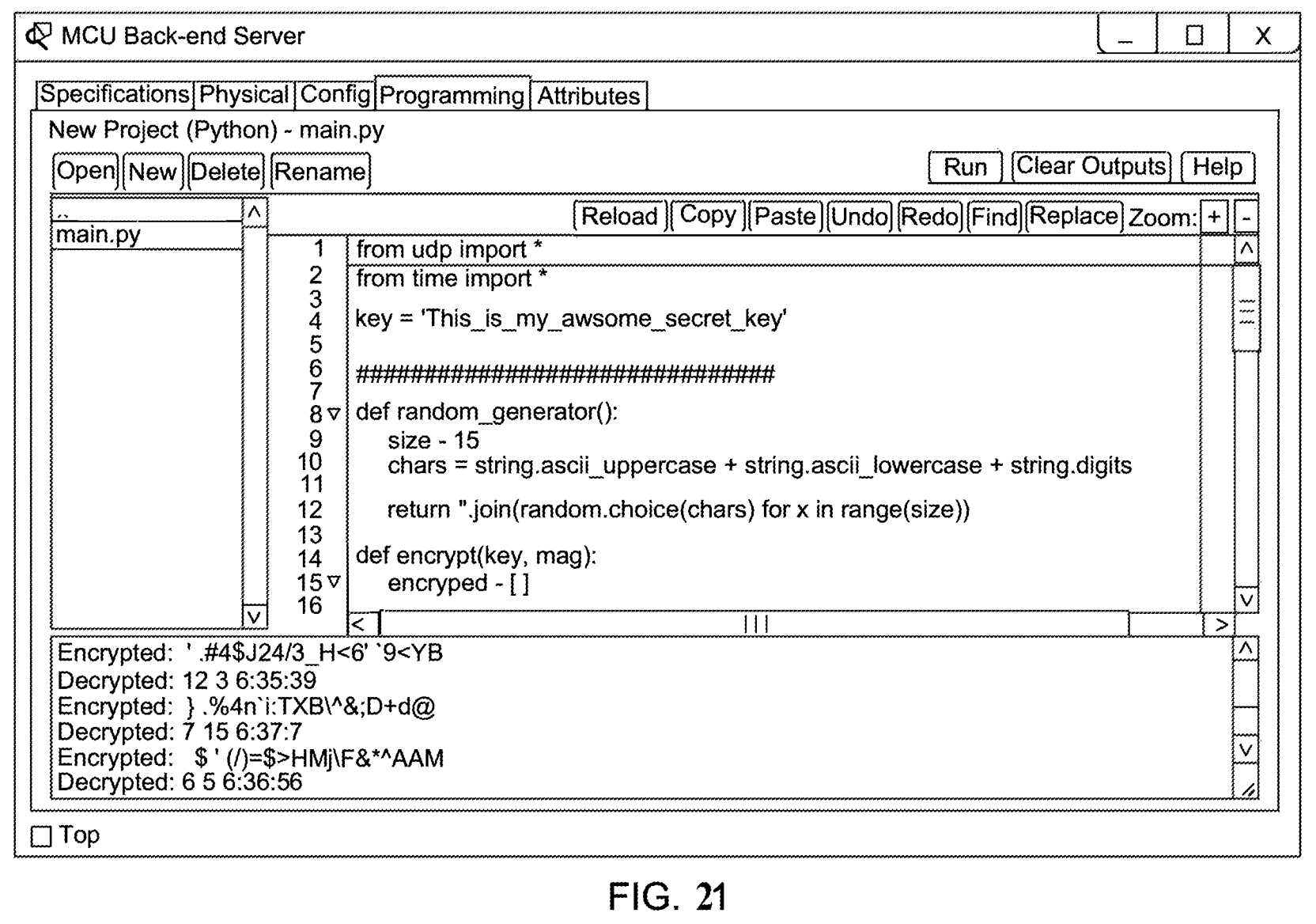

FIG. 21 illustrates a sample of the secure collected data at the back-end server;

FIG. 27 illustrates a valid foreign tag two is read and then updated on the serial monitor; and FIG. 28 illustrates Invalid foreign tag four with signature is not updated.

DETAILED DESCRIPTION

Figure 1:
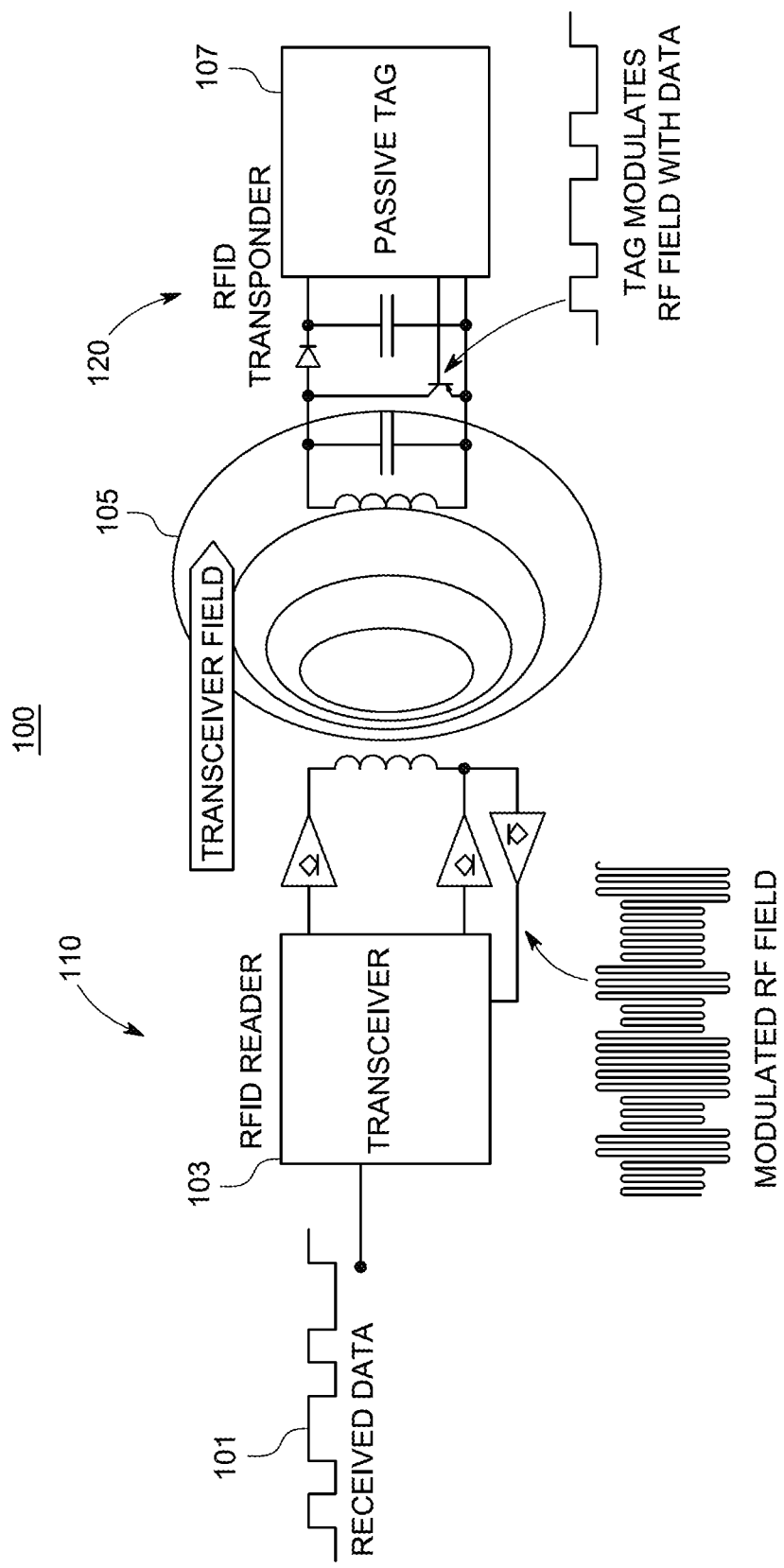
FIG. 1 illustrates a schematic of a typical RFID system.

In the drawings, like reference numerals designate identical or corresponding parts throughout the several views. Further, as used herein, the words "a," "an" and the like generally carry a meaning of "one or more," unless stated otherwise. The drawings are generally drawn to scale unless specified otherwise or illustrating schematic structures or flowcharts.

Furthermore, the terms "approximately," "approximate," "about," and similar terms generally refer to ranges that include the identified value within a margin of 20%, 10%, or preferably 5%, and any values there between.

The combination of a wide variety of sensors, WSN and RFID technologies may be used to build a real-time healthcare monitoring system with very high quality. RFID technology in particular is an important component for the presently disclosed healthcare system due to its energy autonomy and low cost.

Under some circumstances an RFID Reader may not be able to rapidly read data from tags because of its fixed nature and short transmission range. In this way, a high power and a costly RFID Reader may be required to extend the range for quick information gathering. This would bring about an increase in price of an RFID framework taking into account the cost of an RFID Reader (which at present cost may be on the order of $500 or greater) and the costs of initiating connections between back-end servers and the RFID Reader. In this manner, it helpful to limit the quantity of RFID Readers while still accomplishing effective information accumulation.

In typical RFID observing applications, for example, tracking luggage in airlines, a RFID Reader is necessary to rapidly handle several tags at various distances. One solution has been to use a RFID Reader to just read tags within its range. However, many limitations could negatively affect the performance of the data collection such as multi bath fading and limited bandwidth. These issues can be mitigated by transmitting information in short distances through a multi hop information transmission mode in a WSN.

In every data collection system an important challenge relates to real time requirements. Combining RFID Tags with RFID readers and WSNs may help a great deal in solving this challenge. See H. Liu, M. Bolic, A. Nayak, and I. Stojmenovic, "Taxonomy and Challenges of the Integration of RFID and Wireless SensorNetworks," IEEE Netw., vol. 22, no. 6, pp. 26-35, November/December 2008; J. Y. Daniel, J. H. Holleman, R. Prasad, J. R. Smith, and B. P Otis, "Neural WISP: A Wirelessly Powered Neural Interface with 1-m Range," IEEE Trans. Biomed. Circuits Syst., vol. 3, no. 6, pp. 379-387, December 2009; and A. P. Sample, D. J. Yeager, and J. R. Smith, "A Capacitive Touch Interface for Passive RFID Tags," in Proc. IEEE Int'l Conf. RFID 2009, pp. 103-109, each incorporated herein by reference in their entirety.

Subsequently, there are many challenges related to attaining efficient large-scale data collection for healthcare monitoring applications in the case of combining RFID and WSN technologies. Firstly, the transmission must be managed to avoid interference and channel access congestion during the data transmission. Secondly, conventional RFID tags may be susceptible to malicious attack. Finally, it is very important to securely manage the collected data and process it.

The healthcare monitoring method and system of the present disclosure use a hybrid of RFID and WSN data transmission for efficient large-scale data collection. The present disclosure includes a system containing or consisting of three components: smart nodes, RFID readers and a back-end server. The smart node for this system integrates reduced function wireless sensors (sensors without a transmission function) and RFID readers (i.e., an RFID reader with a small range), and RFID tags which work as traditional packet memory buffers for data storage. The smart node is responsible for collecting the body sensed data. Smart nodes that are designated as a cluster head can read its cluster member's sensed data and store this data in its own local tag. All stored information can be sent to the RFID reader through the cluster head. Then, the RFID readers send the collected information to a back-end server for data management and processing. Also, the system incorporates two levels of security algorithms in order to protect data from potential attacks.

The method and system of the present disclosure may include a framework that integrates RFID with wireless sensor network technology based on a clustering scheme to gather information efficiently. The framework may utilize a smart node that contains an RFID tag, reduced function RFID reader and wireless sensor. The clustering scheme selects a cluster head as a smart node which has the highest battery level. The scheme minimizes the total distance between channel heads and channel members and minimizes the number of clusters. In particular, the scheme constructs a cluster based on the choice of the cluster head from smart nodes in the same range. Each smart node can read the tag id and battery level of all smart nodes in its range. The smart node which has the highest battery level will be chosen as the cluster head of this particular cluster. Subsequently, each cluster member in the cluster transmits its tag information to the chosen cluster head. RF ID readers read the tag information from cluster heads. Then, the RFID readers send the collected information to the back-end server for data management and processing. In addition, in order to protect data from potential attacks the framework applies two levels of security algorithms.

The method and system of the present disclosure integrates RFID with wireless sensor networks based on a clustering scheme to collect data in an efficient way may be applied to smart cities, aiming to monitor and collect data related to health condition such as the activity levels, emotional state, and/or physical condition of a large number of people in events such as sporting events, political speeches, concerts, festivals, shopping plazas or malls, airports, train stations, theaters, etc. For purposes of the present disclosure, an event involves people located in a localized area that may be pre-configured with at least one RFID reader. The localized area may be an area that has predetermined boundaries such as an indoor or outdoor sport stadium, concert hall, ballroom or other large room, a fenced-in field, airport terminal building, or theater seating area. The localized area may also be a designated route along streets or paths along which RFID readers may be pre-arranged.

The monitoring and data collection may be related to people participating in the event, such as runners participating in a marathon, cyclists participating in a bicycle race, soccer players playing soccer, or may be related to people in an audience observing the participants. The monitoring and data collection may be for purposes such as observing and/or studying the impact on behavior of persons as they experience various conditions that occur during an event. For example, the monitoring and data collection may be for a study of the behavior of persons over the course of a sporting event, a political speech, concert, or a theater show. A study may be conducted to monitor participants in a sporting event.

Aspects of the method and system of the present disclosure include:

A smart node: A wearable smart node which consists of an RFID tag, a reduced function RFID reader and body/environment sensor.

A healthcare monitoring application based on a clustering scheme. The scheme minimizes the total distance between channel heads and channel members and minimizes the number of clusters.

Efficient collection of health information between nodes in an efficient way for a large-scale system. The resulting clusters derived from the clustering scheme remove the burden from the RFID reader to read every single node, by reading only from the node within its range. This reduces channel access congestion, and thus reduces the interference. Also, reading only a node within its range reduces the transmission delay. Thus, the information is collected between nodes in efficient way for a large-scale system.

Security Policies address data communication security threats with readers in a manner to reduce the privacy and security risks. In particular, in order to protect data from potential attacks the method and system of the present disclosure applies two levels of security algorithms.

Data Collection Technique

Disclosed is a data collection method and system that can efficiently collect a plurality of human beings health parameters (e.g. body temperature, heart rate, blood pressure, muscle activity, location, movement, etc.). The method and system may be used for a large number of persons and makes the data available to a back-end server in real-time. The method and system uses a Hybrid RFID and WSN system that is organized based on clustering scheme that allows for both efficient data collection and data communication. An exemplary system for monitoring the health parameters may be implemented using Cisco Packet Tracer (for example version 7.0) since it supports IoT, RFID, and many other functions, and using an exemplary physical system.

Figure 2:
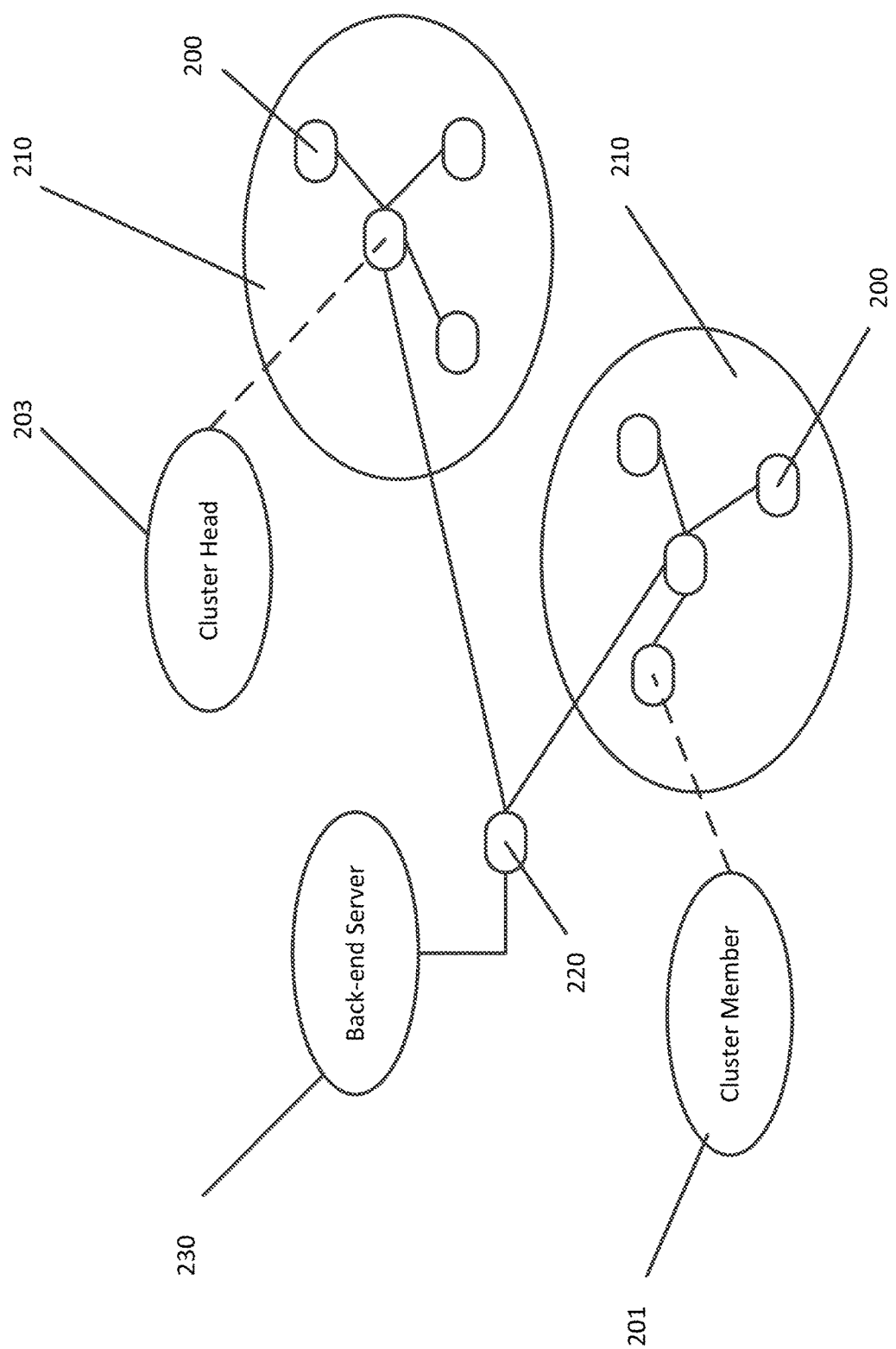
FIG. 2 illustrates the architecture of the healthcare monitoring system in accordance with exemplary aspects of the disclosure.

FIG. 2 illustrates an exemplary architecture of the healthcare monitoring system. The components in the system architecture include smart nodes 200, RFID readers 220, and a back-end server 230 as shown in FIG. 2. The smart nodes 200 are grouped into one or more clusters 210. The smart nodes 200 in each cluster 210 are assigned a role of cluster head 203 and cluster members 201.

The smart node 200 integrates the functionalities of RFID and WSN technologies. For health care monitoring, the smart node 200 may consist of at least one reduced-function Body Sensor (BS), an RFID tag, and a Reduced-Function RFID Reader (RFRR). The BS is reduced function in that it does not have its own transmission function, which is unlike normal wireless sensors. The BS is responsible for collecting the body sensed data such as heart rate, muscle activity and body temperature. The RFRR 103 is an RFID reader with a short communication range. It can read other smart nodes' tags and store this data into its own local tag 107. The RFID tag works as traditional packet memory buffer for data storage.

Figure 3:
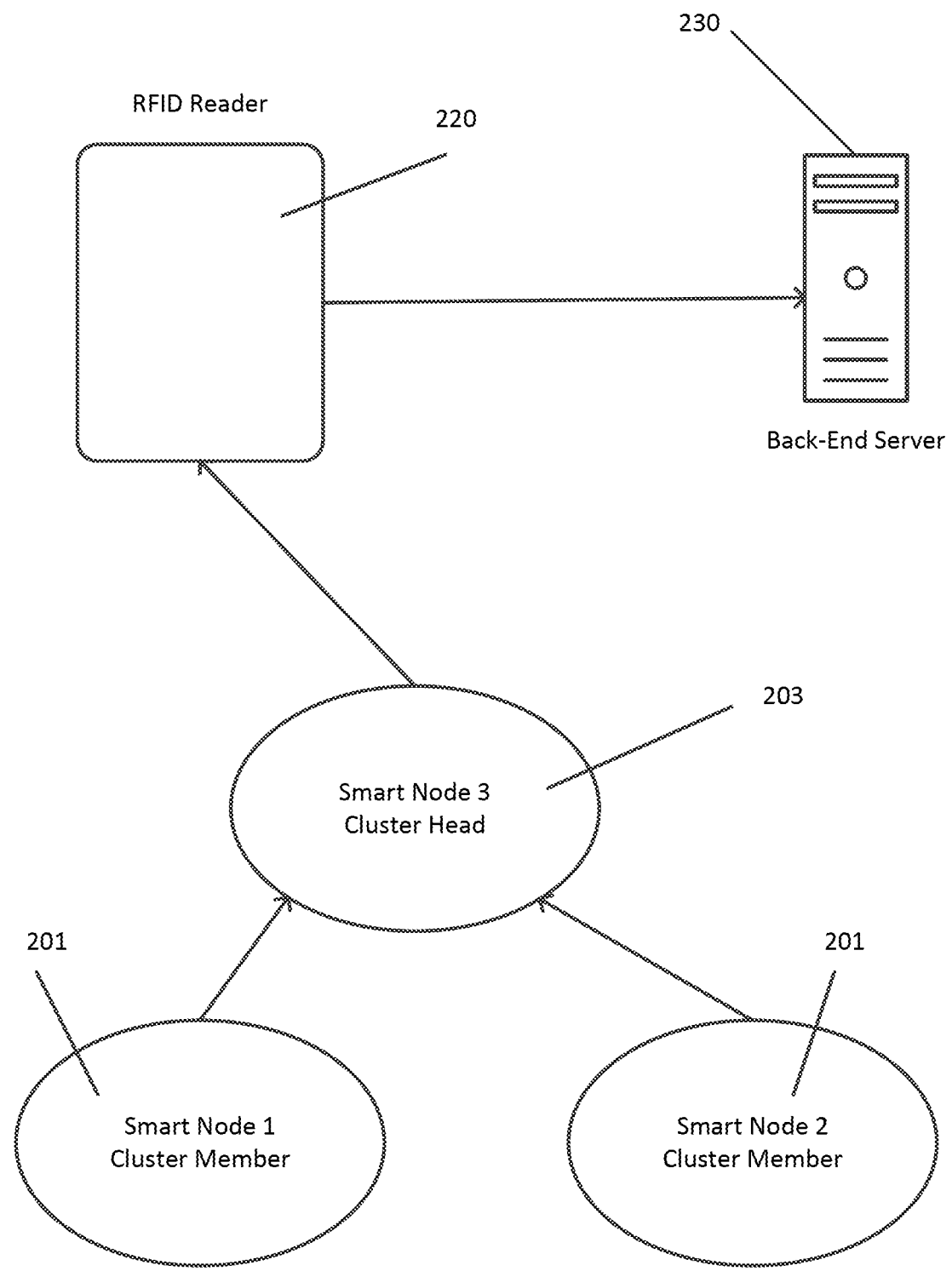
FIG. 3 illustrates a resulting layout of the clustering scheme in accordance with exemplary aspects of the disclosure.

FIG. 3 illustrates the layout of a data transmission path based on a clustering scheme. The construction of a cluster 210 depends on the choice of the cluster head 203 from among smart nodes 200 in the same communication range. In constructing a cluster 210, a cluster head 203 is a smart node that is within RFID range of cluster members 201. Each smart node 200 is configured to read the tag id of all smart nodes in its communication range. As will be described later, the smart node 200 which has the highest battery level will be chosen as the cluster head 203 of this particular cluster 210. The cluster 210 includes cluster head 203 and cluster members 201. The cluster head 203 reads all data packets from the tags of each cluster member 201 and stores the read data packets in its own RFID tag memory. The RFID reader receives all packets of nodes from the cluster head 203, instead of reading every tag when the cluster head moves into the RFID reader range. In some embodiments, RFID readers 220 may be placed at predetermined locations within the localized boundary of an event so that at least one RFID reader 220 will be within communication range of one or more smart nodes 200 during the event. The RFID readers 220 send the collected information to the back-end server 230 for data processing and management. It can be observed from FIG. 3 that the smart nodes 1 and 2 200 send their sensed data to the cluster head 203 (smart node 3). Then, all information can be sent to an RFID reader 220 through the cluster head 203 once it enters the RFID reader's zone. Then, the RFID readers 220 send the collected information to the back-end server 230 for data management and processing.

Figure 4:
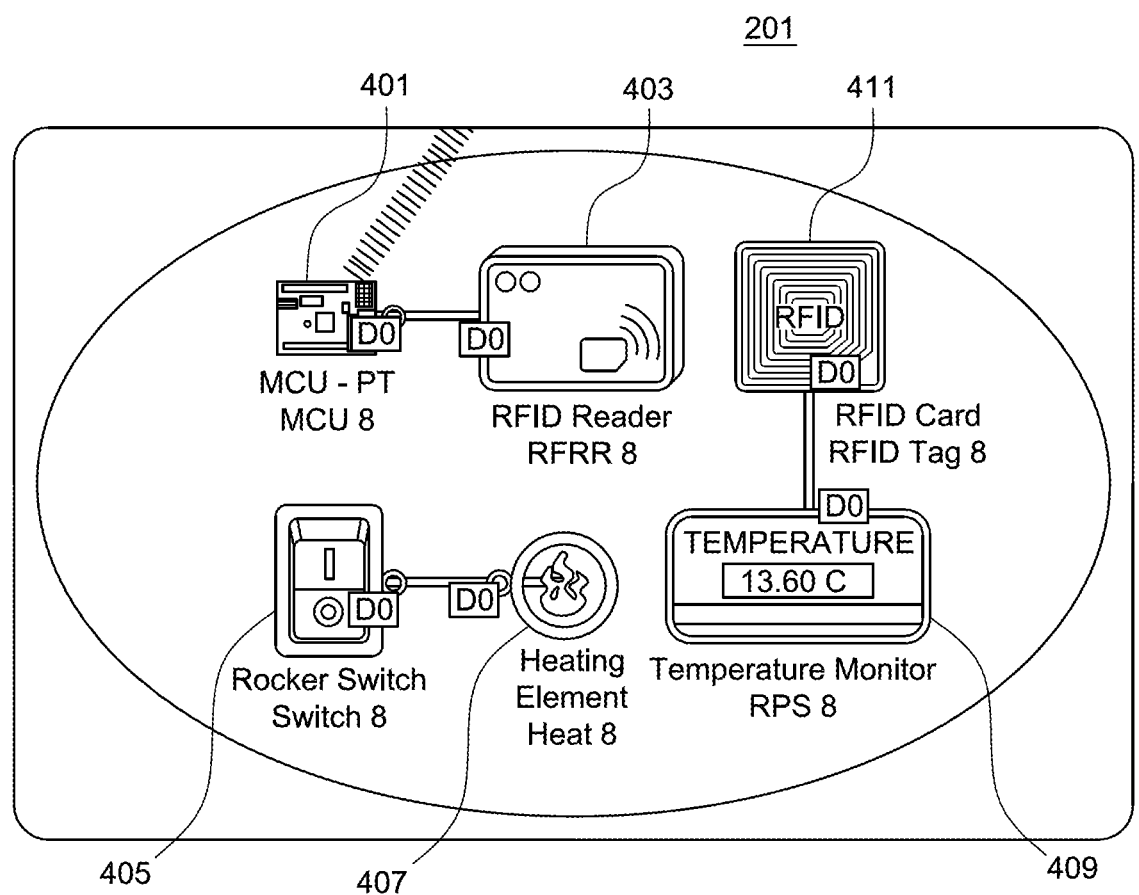
FIG. 4 illustrates exemplary smart node components in packet tracer.
Figure 5:
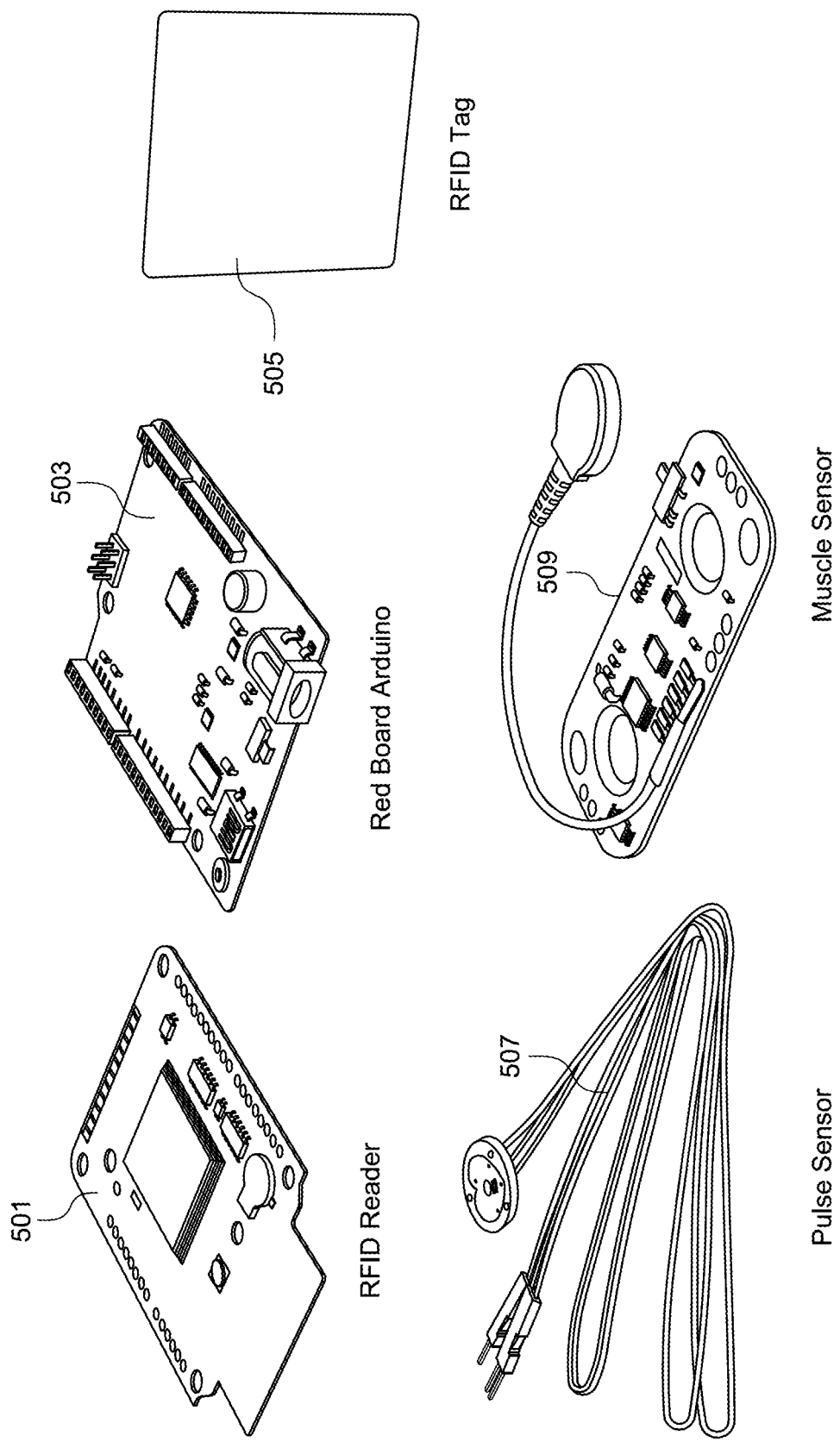
FIG. 5 illustrates exemplary real components of smart nodes.

FIG. 4 and FIG. 5 show exemplary smart node components in Cisco Packet Tracer and as real physical components, respectively. In some embodiments, the smart nodes 200 are a hybrid of a sensor network node and an RFID tag. A smart node 200 includes a reduced-function RFID reader as its antenna and radio transceiver, a microcontroller that includes a processing circuitry, power source, and electronic circuit for interfacing with sensors, an RFID tag, and one or more sensors. The exemplary smart node 200 in Cisco Packet Tracer consists of RFRR 403, BS 409 (e.g., a body temperature monitor), RFID Card 411 and a microcontroller 401 (503). The smart node components in Packet Tracer may also include a Heating Element 407 and an associated Rocker Switch 405. Exemplary physical components may include an RFID Reader 501, an Arduino compatible processor board 503, an RFID Tag 505, a Pulse Sensor 507, and a Muscle Sensor 509.

The RFRR 501 may be a normal RFID reader with a short communication range. For example, the RFRR 501 may be an RFID Reader Module (for example, from Sparkfun Electronics) that can read within a short range of from approximately 30 to 60 centimeters. See The Sparkfun specification for an RFID reader, (sparkfun.com), incorporated herein by reference in its entirety. The RFRR 501 may be programmed to perform two tasks; the first task is reading the heart beat and the muscle sensed data from the BS (pulse sensor 507 and muscle sensor 509), respectively and store these data into its own RFID tag 505. The second task is reading the data from other smart nodes within its transmission range and storing it into its RFID tag 505.

The BS 409 is reduced-function as it does not have its own transmission function, unlike the normal sensors. It is responsible for collecting the body sensed data such as heart rate and muscle activity. Exemplary sensors include a pulse sensor 507 (e.g., Pulse Sensor Amped available at Sparkfun) and a muscle sensor 509 (e.g., MyoWare Muscle Sensor). The pulse sensor 507 may include an optical heart rate sensor with amplification and noise cancellation circuitry. The pulse sensor 507 may be attached to an earlobe or finger tip to sense heart rate. The muscle sensor 509 may include an electromyography sensor to measure the electrical activity of a muscle, outputting a voltage that is dependent on the amount of activity in a selected muscle. The muscle sensor 509 includes one or more electrodes that are to be stuck to selected muscles.

Other sensors may include a blood pressure sensor, a location sensor (e.g., GPS), and an accelerometer (to sense sudden movement and movement direction). These body sensors may be used to monitor/observe and the IoT devices can be utilized for observing physical or ecological conditions, etc. In some embodiments, devices and/or techniques may detect cancer using simple vital signs obtained from these body sensors.

Smart nodes 200 equipped with body sensors such as a body temperature monitor 409, and/or the pulse sensor 507 and the muscle sensor 509 may provide health condition information on the activity levels, emotional state, or physical condition of a large number of people or individuals in a group of people. For example, people in an audience at a concert, political speech, theater show may be monitored to study activity levels or emotional state (via pulse rate and/or muscle activity) over the course of the event. Participants in a sporting event may be monitored to study activity levels or physical condition (pulse rate and/or muscle activity) over the course of the sporting event. Information obtained from smart node sensors on participants of a sporting event may be used to detect a participant that is exceeding health-related parameters, such as high body temperature (higher than normal body temperature by a predetermined threshold) and/or high heart rate (higher than a predetermined threshold).

The RFID tag 505 may function as a traditional packet memory buffer for data storage. The RFID tag 505 typically includes an integrated circuit and a non-volatile memory. RFID tags 505 are typically configured to store up to 2 kilobytes of data.

An Arduino compatible processor board 503 may be for example, SparkFun RedBoard, and include a microprocessor programmable with Arduino. The microprocessor may be programmed to monitor, verify and process smart node readings. The processor board 503 preferably includes necessary digital I/O pins and analog inputs for connecting the sensors.

In some embodiments, the data transmitted between smart nodes 200 and RFID readers 220 may be structured to include three fields, including, a first filed to contain a smart node ID which belongs to specific user or smart node, a second field to contain the sensed data and a third field to contain a sequence number of the data to aid in determining when the data was updated. The smart node ID may be a unique identifier that is stored in the tag when the tag is produced. The sequence number may be an integer value that is associated with data as it is stored. In one embodiment, the sequence number may be a time stamp having a value that represents time and date.

Figure 6:
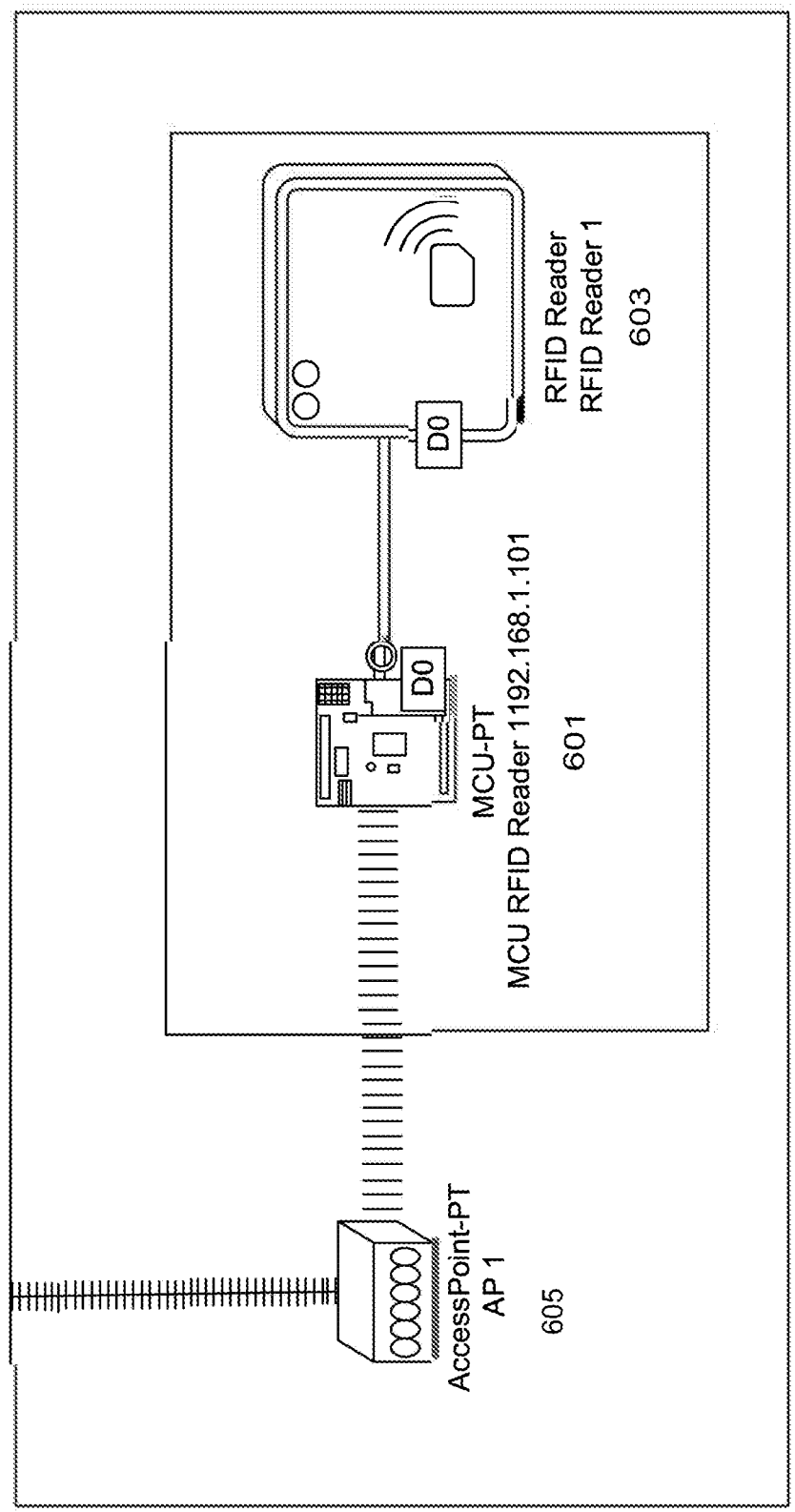
FIG. 6 illustrates exemplary components of the RFID reader and its connectivity with the back-end server.

FIG. 6 shows the components of an exemplary RFID reader and its connectivity with the back-end server. The RFID readers 220 are responsible for reading the data from the smart nodes 200 and delivering it to the back-end server 230. The transmission range of the RFID reader 220 is much greater than that of the RFRR 403 (501). In some embodiments, RFID readers 220 may be placed at predetermined locations within the localized boundary of an event so that at least one RFID reader 220 will be within communication range of one or more smart nodes 200 during the event. When reading the data of a smart node tag, it may send that data directly to the back-end server 230 wirelessly using UDP socket. Regarding FIG. 6, an RFID reader 220 may include a microcontroller 601 (MCU) interconnected with an RFID reader 603. The microcontroller 601 may communicate with the back-end server 230 by way of an Access Point 605 (e.g., UDP access point). The RFID reader 603 is characterized by operating frequency, reader distance, and data transfer rate. Operating frequency of RFID readers is typically 120 to 150 kHz or 13.56 MHz. Other readers of much higher frequencies are possible. Reader distance of RFID readers is typically a few centimeters (e.g., 20 CM), and up to approximately 1 meter.

Figure 7:
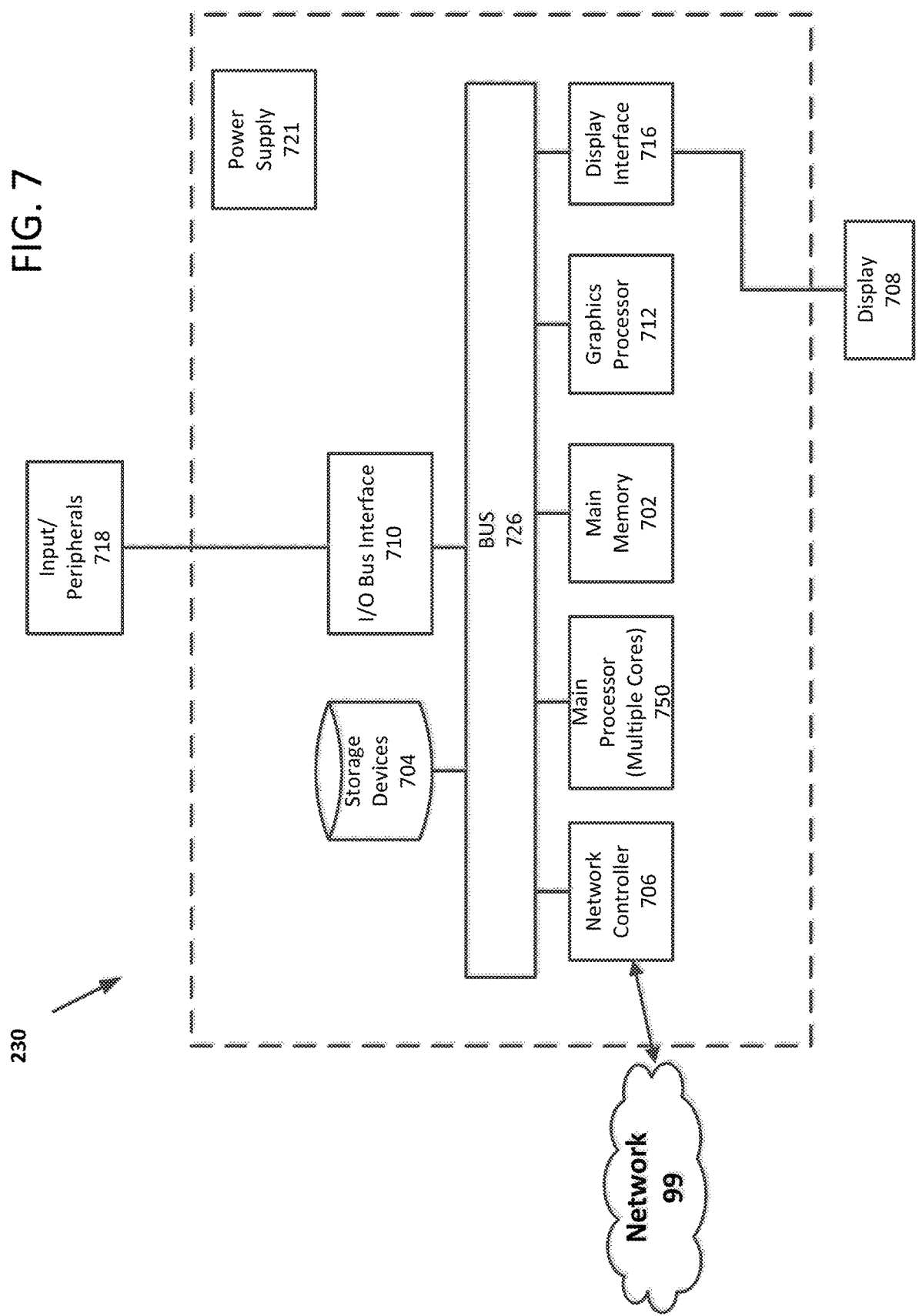
FIG. 7 is a block diagram illustrating an example computer system for a backend server.

FIG. 7 is a block diagram illustrating an example computer system for a backend server 230 for implementing the clustering method according to an exemplary aspect of the disclosure. The computer system may be a server or workstation running a server operating system, for example Windows Server, a version of Unix OS, or Mac OS Server. The computer system 700 may include processing circuitry, such as one or more processing cores 750 and a graphics processor 712. The graphics processor 712 may perform many of the mathematical operations. The computer system 700 includes main memory 702, typically random access memory RAM, which contains the software being executed by the processing cores 750 and graphics processor 712, as well as a non-volatile storage device 704 for storing data and the software programs. Several interfaces for interacting with the computer system 700 may be provided, including an I/O Bus Interface 710, Input/Peripherals 718 such as a keyboard, touch pad, mouse, Display Interface 716 and one or more Displays 708, and a Network Controller 706 to enable wired or wireless communication through a network 99. The interfaces, memory and processors may communicate over the system bus 726. The computer system 700 includes a power supply 721, which may be a redundant power supply.

Figure 8:
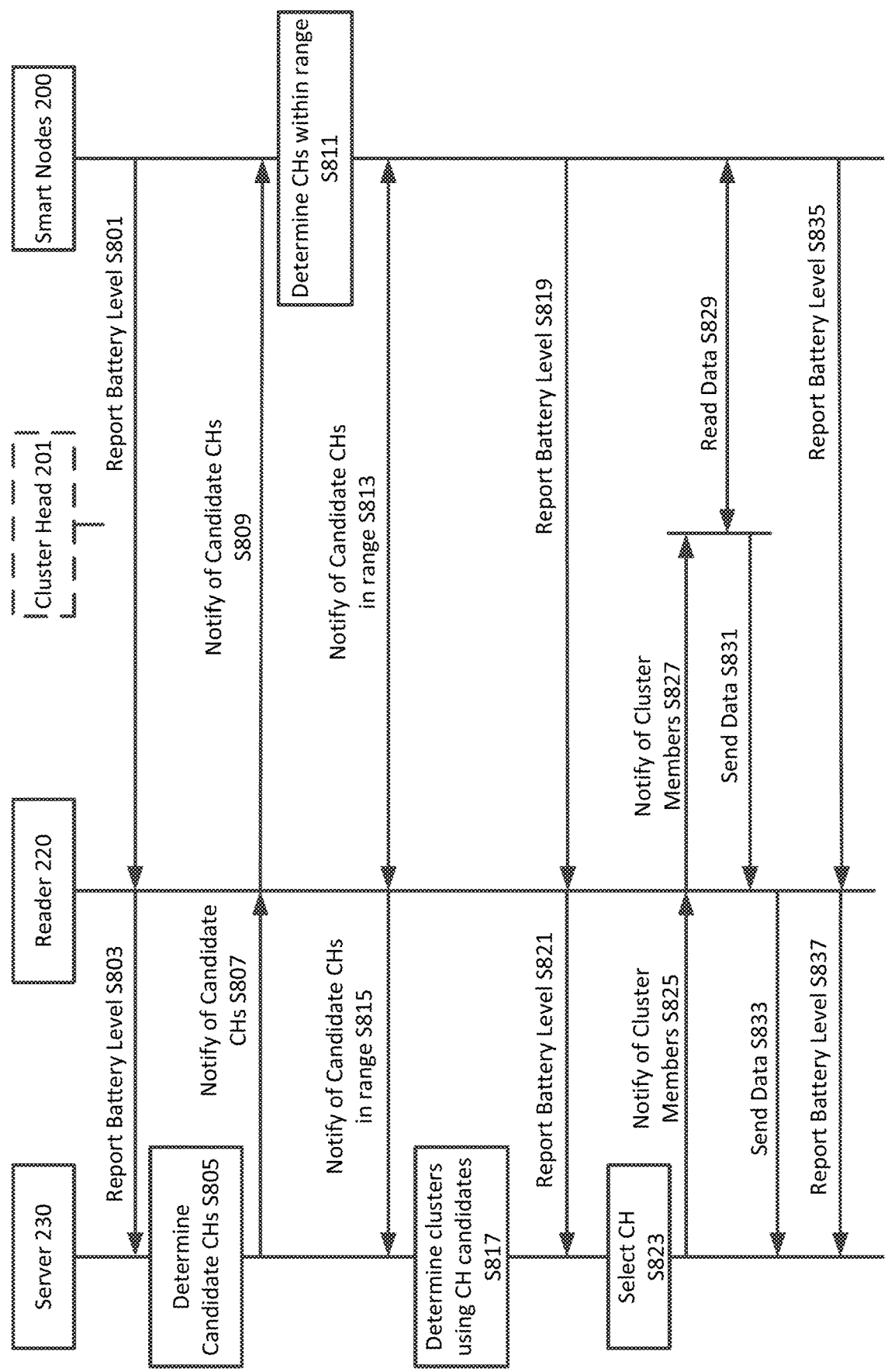
FIG. 8 is a sequence diagram for a method of transmitting data using a clustering scheme in accordance with exemplary aspects of the disclosure.

FIG. 8 is a sequence diagram for a method of transmitting data using a clustering scheme in accordance with exemplary aspects of the disclosure. Although the diagram shows a scheme in which the RFID reader sends the collected data packets to the back-end server 230 for data processing and management, the approach is not limited to this sequence of operations. A scheme may be performed within the RFID network where one capable smart node device collects this data and makes a decision. In addition, the scheme may be autonomous such that as every smart node hears each other, the smart node having the highest battery will be known by all smart nodes and that smart node may announce itself to others, so they can join its cluster. These alternative approaches save energy and communication traffic.

To form the clusters in the clustering scheme, smart nodes 200 report their battery levels to the server 230 through the RFID readers 220. In some embodiments, the smart nodes 200 report their battery level on a periodic schedule, for example, every minute, every five minutes, every hour. In some embodiments, the smart nodes 200 may report their battery level each time the battery level reaches a predetermined percentage, for example, at 75%, 50%, 25%, or at intervals of every 10% reduction in level. Smart nodes 200 report their battery level to the backend server 230 (S803) via an RFID reader 220 (S801). In S805, the back-end server 230 checks the battery level of the smart nodes 200 to determine candidate nodes that may serve as cluster heads. For example, the backend server 230 may choose smart nodes 200 that have a battery level of at least 50% as candidate cluster head nodes. In S807, the backend server 230 will send a notification message to the RFID reader 220 of a list of chosen candidate cluster head nodes, which are then sent by the RFID reader 220 to the smart nodes 200. In S811, the smart nodes 200 may determine which of the candidate cluster nodes are within communication range of the respective smart node 200.

In S813, the smart nodes S811 may transmit a message to the RFID reader 220 to notify which candidate CHs are within communication range. In S815, the RFID reader 220 then transmits a message containing this set of candidate CHs to the backend server 230. In some embodiments, the candidate CHs are identified by an ID number that is stored in their tag. In some embodiments, the smart nodes 200 may transmit their determined CHs by sending a message to one of the candidate CHs, which forwards the message to the RFID reader 220.

In some embodiments, the RFID reader 220 may read candidate CHs within communication range from the tags of the smart nodes 220 after a predetermined amount of time from sending the full list of candidate CHs. The predetermined amount of time may be a fraction of a second, to a few seconds, or longer.

In some embodiments, cluster members 201 in each cluster 210 are at fixed positions in which the distance between cluster members and candidate cluster heads CHs 203 remain unchanged. In such case, the determination of clusters in S817 may be performed based on an initial set of distances between cluster members 201 and candidate CHs 203 without repeated communication from cluster members 201 to provide updated candidate CHs 203 within communication range.

In S817, the backend server 230 performs a clustering scheme to group smart nodes 200 into clusters based on the candidate CHs provided from smart nodes 220. Depending on when battery levels are reported, the backend server 230 may receive battery level reports (S819, S821) while it is determining clusters, or before CHs are determined.

In S823, a smart node 200 may select a CH 203 within its communication range based on a determination of a candidate CH that has the highest battery level in a cluster 210.

In S825, the backend server 230 may send a message to the RFID reader 220 to notify the selected CHs of the cluster members 201 in the respective cluster 210. In S827, the RFID reader 220 forwards the message to the CHs 203. In some embodiments, the backend server 230 may send individual messages for each selected cluster head 203, or may send several messages depending on the number of cluster members 201 in a cluster 210.

In S829, each CH 201 reads sensor data from tags of cluster members 201 in its cluster.

In S831, the CHs 203 send the collected data to the RFID reader 220. In S833, the RFID reader 220 sends the collected data to the backend server 230 for management and storage. During this process, smart nodes 200 may continue to report their battery level (S835, S837) to the backend server 230, in which case, revised candidate CHs may be determined, and the process is repeated starting from S805.

In some embodiments, the backend server 230 is initially provided with the position of the smart nodes 200 and RFID readers 220 and receives battery level readings from each smart node 200. The backend server 230 performs the clustering scheme to determine clusters (S817). Then, to select CHs 203, each smart node 200 in a cluster 210 reads the tag id of all smart nodes 200 in its communication range. The smart node 200 which has the highest battery level will be chosen as the cluster head 203 of this cluster 210. The smart node that is selected as CH will announce its election to all its neighboring nodes within communication range, and then these nodes will attempt to join the closest CH node. Then, in S829, the chosen cluster head reads data packets from tags of each member 201 in the cluster. Afterward, in S831 the RFID reader 220 receives all packets from the cluster head 203, and in S833 the RFID reader 220 sends the packets to the backend server 230.

Figure 9:
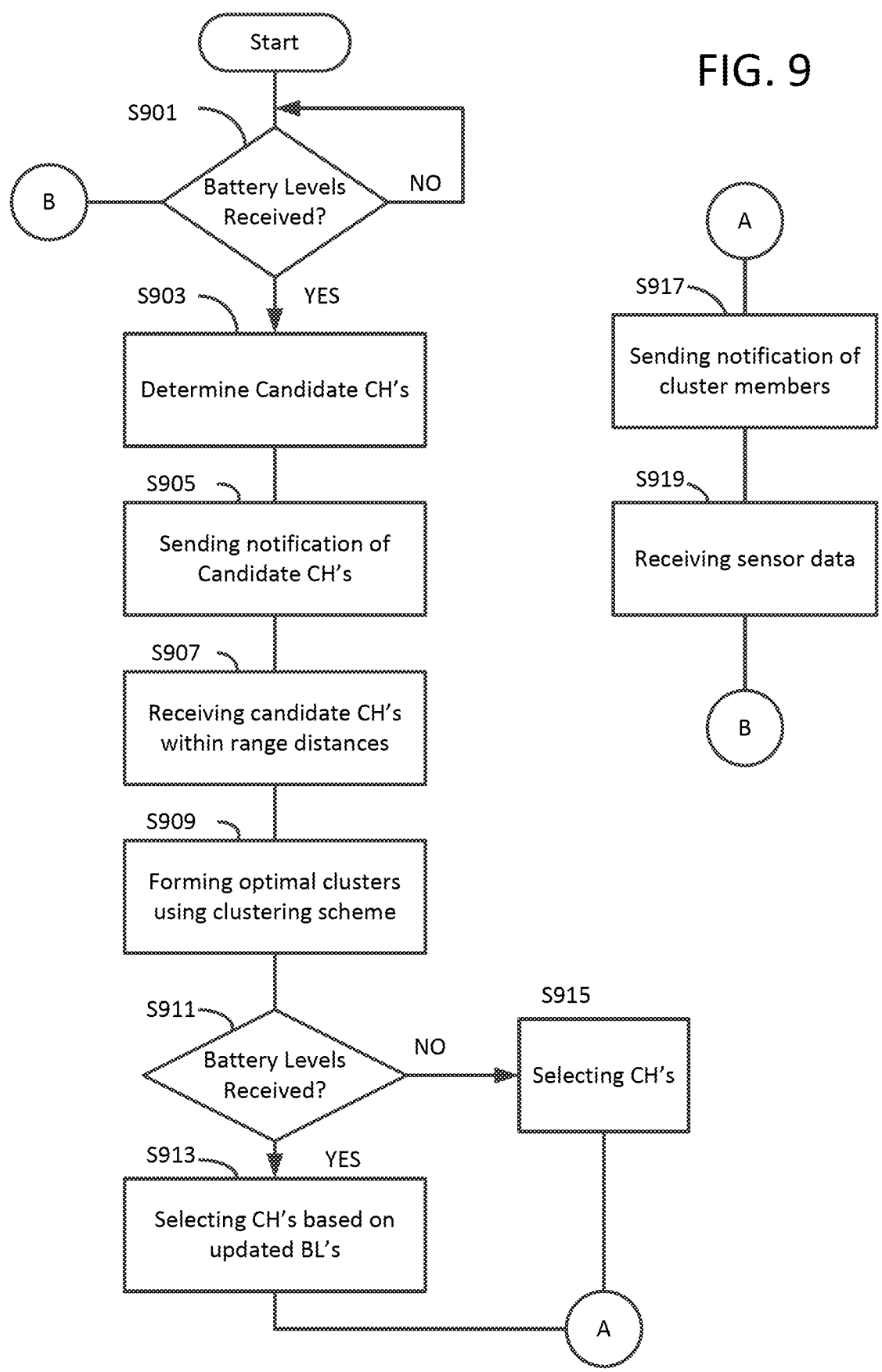
FIG. 9 is a flowchart for a clustering scheme performed by the backend server in accordance with exemplary aspects of the disclosure.

FIG. 9 is a flowchart for a clustering scheme performed by the backend server in accordance with exemplary aspects of the disclosure. In embodiments of the disclosure, the backend server 230 performs a clustering scheme that takes into consideration the battery levels of smart nodes 200. Cluster members 201 having the highest battery level are selected as cluster heads 203 of clusters 210. In S901, the backend server 230 listens for messages from the RFID readers 220 that contain battery levels for associated smart nodes 200, identified by their tag ID. As battery levels are received (YES in S901), the backend server 230 may begin to group smart nodes 200 into candidate CHs based on a battery level that is at least a predetermined percentage, such as at least 50% battery level. In some embodiments, the backend server 230 may continue to determine candidate CHs until it has received battery level information from all smart nodes 200. In some embodiments, the backend server 230 may collect information on battery level from the smart nodes 200 for a predetermined period of time, for example one minute, five minutes, an hour.

In S905, once the backend server 230 has determined a group of candidate CHs, the backend server 230 will send one or more messages to notify smart nodes 200 of candidate CHs. In S907, the backend server 230 will receive messages that indicate candidate CHs for respective smart nodes 200. In some embodiments, the message may include an ID for the smart node 200, and a list of IDs for candidate CHs that are within communication range of the smart node 200. In some embodiments, the message may include a distance between the smart node 200 and each candidate CH.

In some embodiments, the position of smart nodes 200 in clusters 210 may remain unchanged over a substantial period of time because they are at fixed locations. In such case, the step S905 and S907 may not be required, or may only be required one time to obtain initial distance values between cluster members 201 and candidate cluster heads CHS 203.

In S909, the backend server 230 may perform a clustering scheme to form optimal clusters. The clustering scheme will be described in further detail below. As the backend server 230 performs the clustering scheme, or before all CHs have been selected, the backend server 230 may continue to receive messages containing battery levels of smart nodes 200. In S911, the backend server 230 will determine if more battery level messages have been received. If additional battery level messages have been received (YES in S911), in S913, the backend server 230 will select CHs for each cluster based on the most current battery level. The CHs 203 with the highest battery level for each cluster 210 will be selected. If no further battery levels have been received (NO in S911), in S915, the CHs 203 with the highest battery level for each cluster will be selected. In the case of a tie, where two candidate CHs in a cluster 210 have the same highest battery level, a CH may be selected based on which battery level was reported first.

In S917, the backend server 230 sends one or more notification messages to inform CHs 203 of the cluster members 201 that are contained in their respective cluster 210, In S919, the backend server 230 will receive sensor data that had been collected by the CHs 203.

Figure 10:
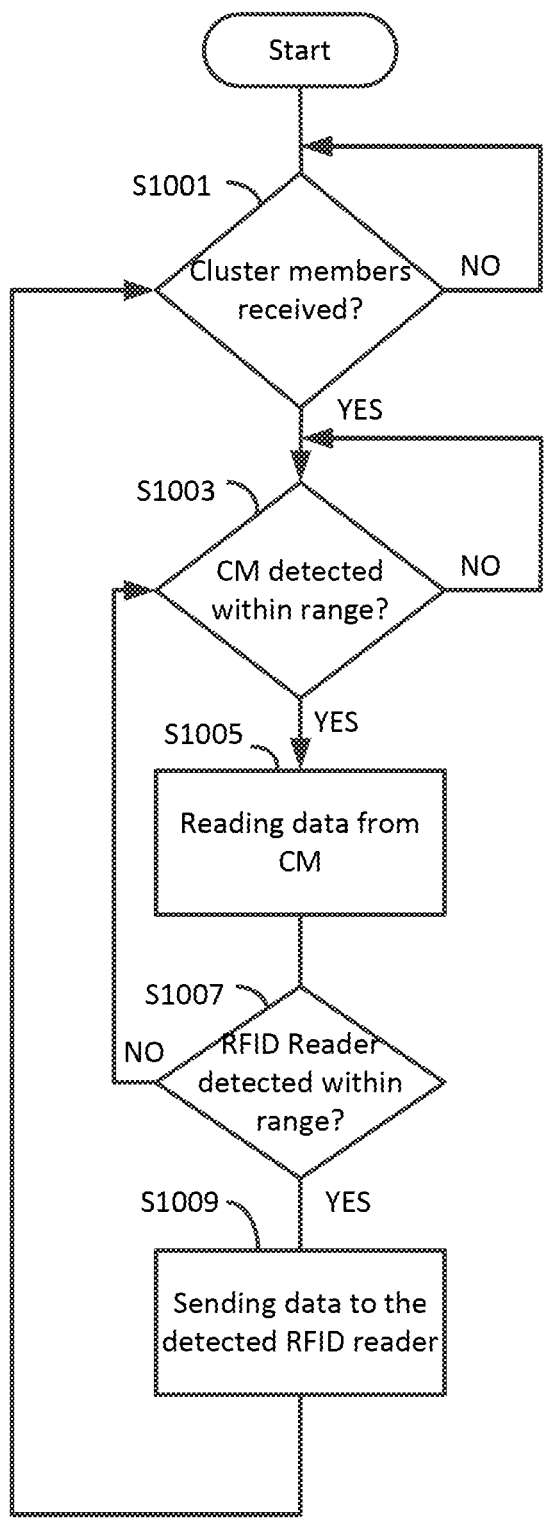
FIG. 10 is a flowchart for a method of transmitting data by a cluster head determined by the clustering scheme in accordance with aspects of the disclosure.

FIG. 10 is a flowchart for a method of transmitting data by a cluster head determined by the clustering scheme in accordance with aspects of the disclosure. In embodiments of the disclosure, CHs 203 are selected for each cluster 210 based on battery level. The CHs 203 are notified by the backend server 230 of the cluster members 201 that make up their respective cluster 210. CHs 203 may then seek out cluster members 201 that are within communication range, or as they come into communication range of the CH 203. In S1001, a smart node 200 may receive a message from a RFID reader 220 that contains cluster members 201 that the backend server 230 has determined to be within a cluster 210 and indicating that the smart node 200 is a CH. Once informed of status as a CH 203, in 51003, the CH 203 begins to detect cluster members 201 in the provided list that are within communication range, or as they come into communication range of the CH 203. As cluster members 201 are detected as being in range, in S1005, the CH 203 reads sensor data from the tag of the cluster member 201.

In some embodiments, the CH 203 may continue to read data from cluster members 201 in its cluster 210 until it reaches maximum capacity (in some embodiments, the capacity of a smart node tag is data from 11 cluster members 201. In some embodiments, the CH 203 may listen for an RFID reader 220, and when an RFID reader 220 is detected within communication range of the CH 203 (YES in S1007), in S1009, the CH 203 will send its data to the detected RFID reader 220. In some embodiments, the RFID reader 220, having greater communication range, may periodically read from tags of CHs 203.

A. Data Structure

In one embodiment, for each smart node 200, three packets of data are published so that other nodes can get its information. The three packets of data amount to four (4) bytes of data, including the node ID (1 byte), medical sensor information (1 byte), such as heart rate, and sequence number (2 bytes). Sequencing a node's data keeps a record of how recent the information is and helps other nodes in deciding whether to record a newly read data or discard it.

In the one embodiment, each RFID tag has a 64 bytes capacity. To utilize that capacity, the first 48 bytes are divided into chunks of 4 bytes that each are used to store information of one node. These 4 byte chunks of the 48 bytes amount to a total of 12 data slots. The remaining 16 bytes are used for authentication. The first data slot is reserved for the local RFID tag. The other 11 data slots are initially marked as available. That is they do not contain data from other nodes and are ready to be utilized for that purpose. Each data slot hold the three packets of data including a node ID, sensor data, and a sequence number.

It should be understood that RFID tags may be of other capacities. Also, in some embodiments, the RFID tags may be of different capacities.

Figure 11:
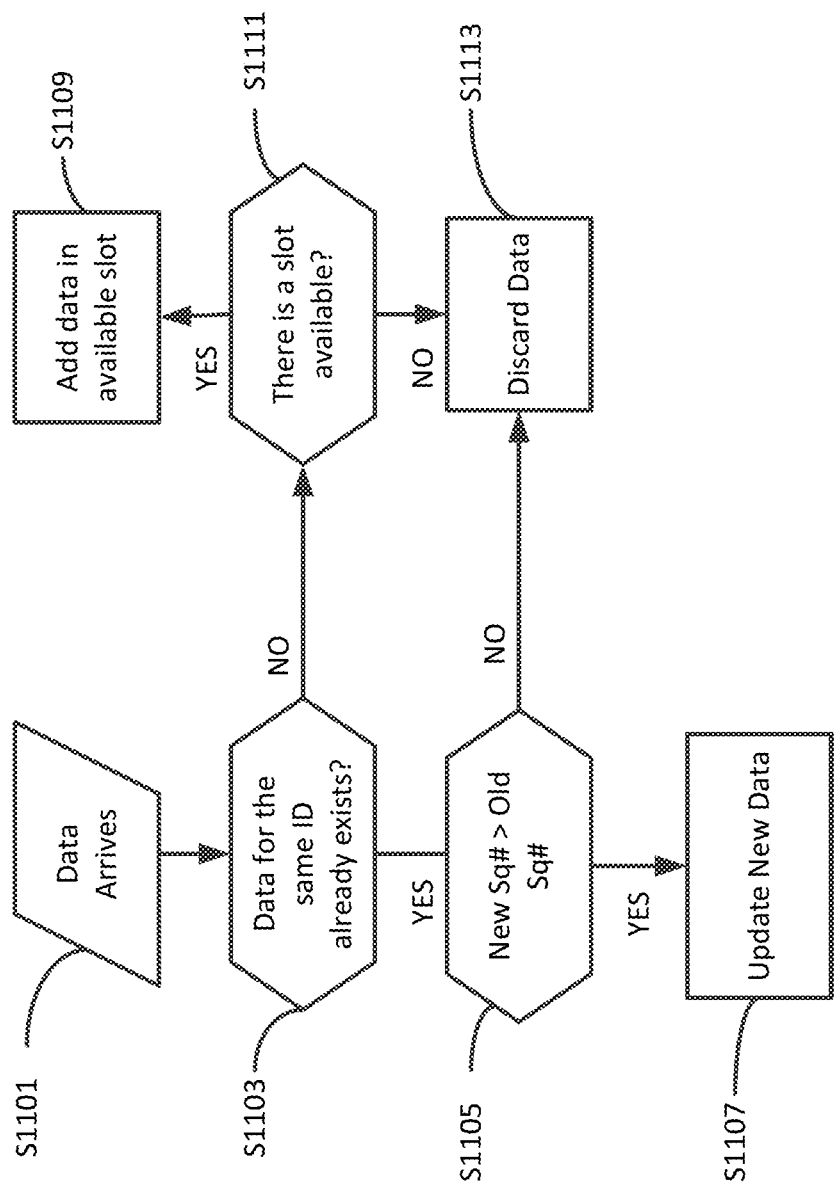
FIG. 11 is a flowchart of a process of handling new data by a cluster head in accordance with exemplary aspects of the disclosure.

FIG. 11 shows a flowchart that represents the process of handling new data. In some embodiments, the process of handling new data is performed in a CH. When a new data arrives in a CH 201, S1101, and is to be stored, in S903, the CH will try to find whether a slot that contains data for the same node ID exists. If so, (YES in S903) in S905, the slot will be updated, in S907, if the sequence number is less than the new sequence number, otherwise (NO in S905), in S913, the new data is discarded. If the CH does not find a previous record for that node ID (NO in S903) in S909, it will store its data in a new available slot (YES in S911), unless all slots are occupied (NO in S911), in which there is no more room for new node data to be stored.

In some embodiments, the sequence number is a time stamp that includes an encoded date and time.

Figure 12:
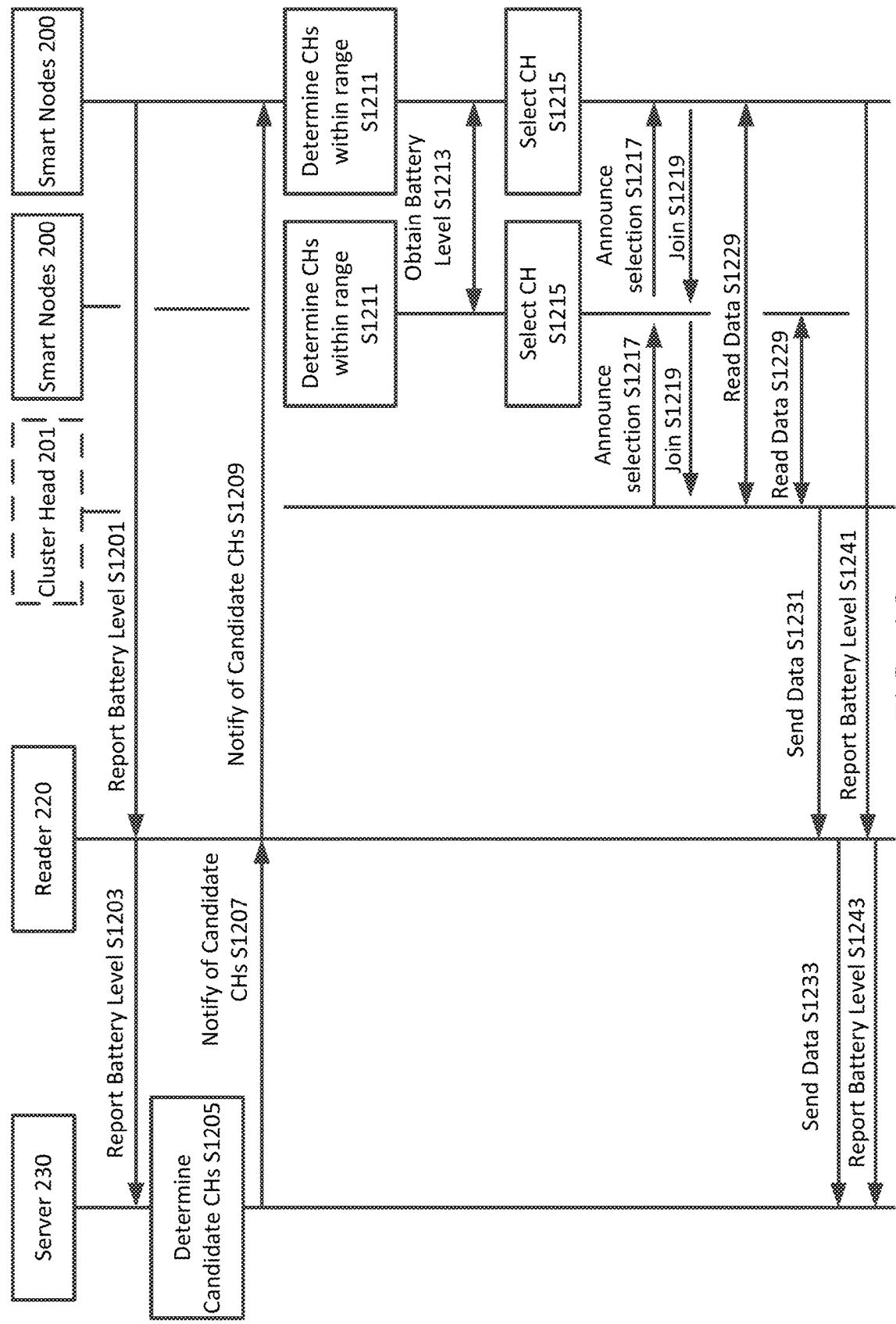
FIG. 12 is a sequence diagram for an alternative method of transmitting data using a clustering scheme in accordance with exemplary aspects of the disclosure.

FIG. 12 is a sequence diagram for an alternative method of transmitting data using a clustering scheme in accordance with exemplary aspects of the disclosure.

Smart nodes 200 periodically report their battery level to the backend server 230 (S1203) via an RFID reader 220 (S1201). In S1205, the back-end server 230 checks the battery level of the smart nodes 200 to determine candidate nodes that may serve as cluster heads. For example, the backend server 230 may choose smart nodes 200 that have a battery level that is above the average of all battery levels, or may choose smart nodes that have a battery level of above a certain level, such as 50%, as candidate cluster head nodes.

In S1207, the backend server 230 will send a notification message to the RFID reader 220 of a list of chosen candidate cluster head nodes, which are then sent by the RFID reader 220 to the smart nodes 200 (S1209). In S1211, the smart nodes 200 may determine which of the candidate cluster nodes are within communication range of the respective smart node 200. In some embodiments, the communication range may be a distance of within 2 feet.

In S1213, smart nodes 200 within communication range may communicate battery levels among each other, and the smart node 200 with the highest battery level will be known by these smart nodes 200.

In S1215, a smart node 200 may select a CH 201 within its communication range based on a determination of a candidate CH that has the highest battery level.

The smart node that is selected as CH will, in S1217, announce its election to all its neighboring nodes within communication range, and then, in S1219, these nodes will attempt to join the closest CH node to form a cluster. Then, in S1229, the chosen cluster head reads data packets from tags of each member 201 in the cluster as collective sensor data. Afterward, in S1231 the RFID reader 220 receives the collective sensor data from the cluster head 203, and, in S1233, the RFID reader 220 sends the packets of collective sensor data to the backend server 230.

During this process, smart nodes 200 may continue to periodically report their battery level (S1241, S1243) to the backend server 230, in which case, revised candidate CHs may be determined, and the process is repeated starting from S1205. The rate at which battery level is reported may be predetermined and may be based on the type of event that is being monitored. For example, in some events, people being monitored may be highly dynamic so that it would be preferable to update battery level information frequently, such as every 5 minutes. Other events, people being monitored may be more static so that it may be preferable to update battery level information less frequently, such as every hour.

Figure 13:
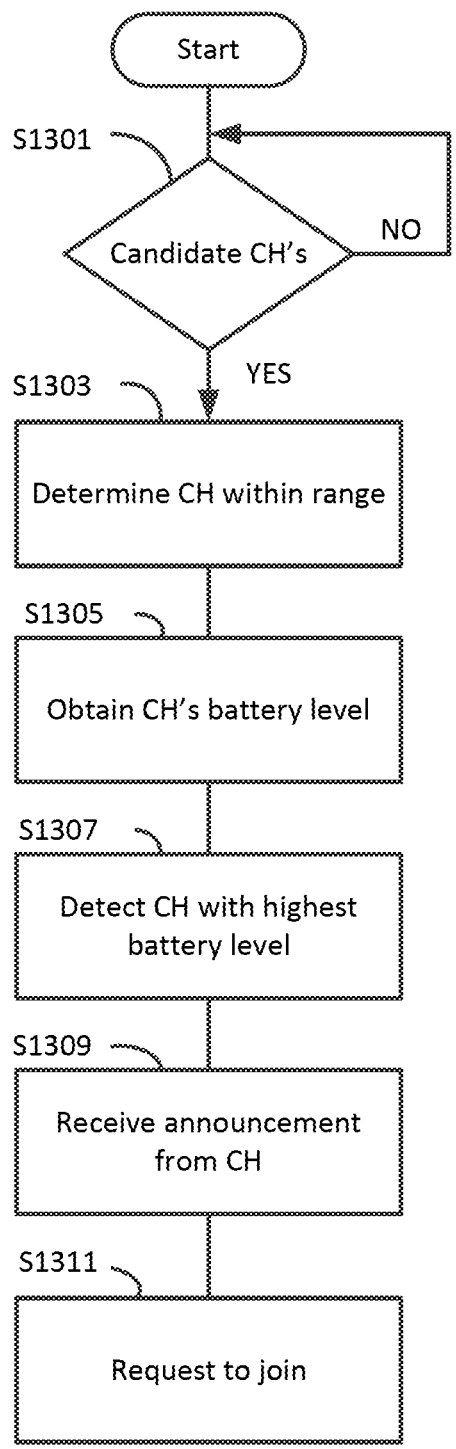
FIG. 13 is a flowchart for a clustering scheme performed by the smart nodes 200 in accordance with exemplary aspects of the disclosure.
Figure 14:
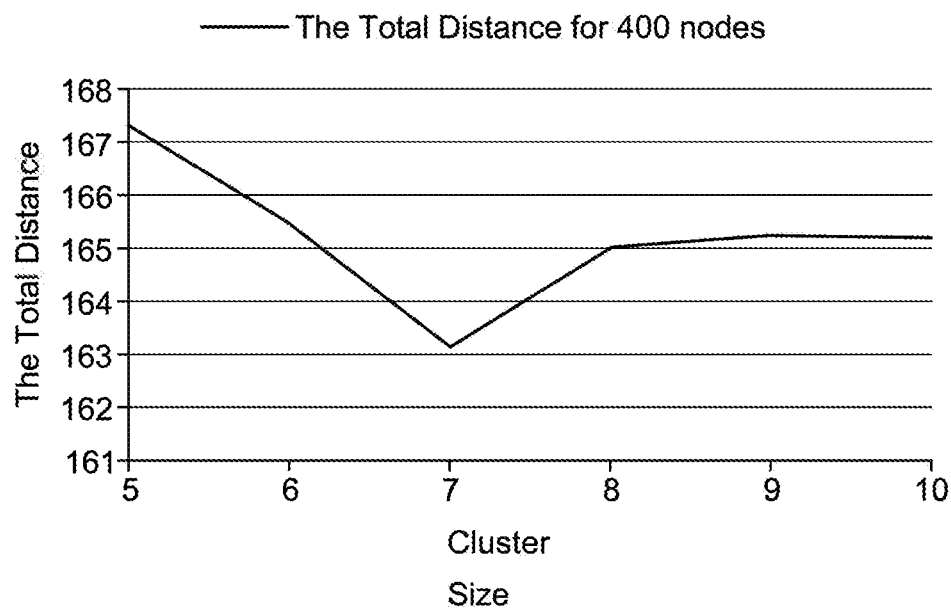
FIG. 14 is a graph illustrating the total distance when changing CS for 400 nodes.
Figure 15:
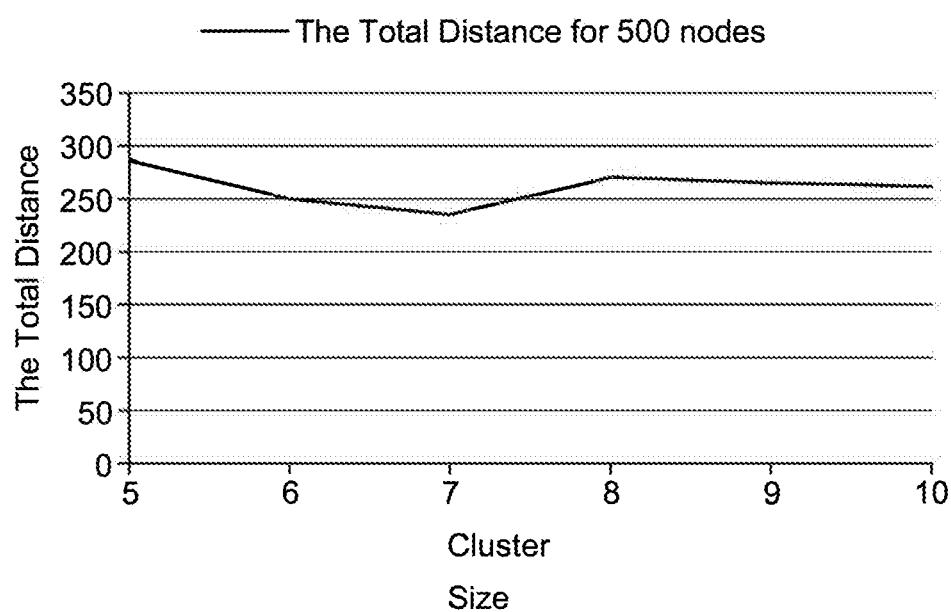
FIG. 15 is a graph illustrating the total distance when changing CS for 500 nodes.

FIG. 13 is a flowchart for a clustering scheme performed by the smart nodes 200 in accordance with exemplary aspects of the disclosure. In embodiments of the disclosure, the smart node 200 performs a clustering scheme that takes into consideration the battery levels of smart nodes 200.

Once the backend server 230 has determined a group of candidate CHs, in S1301, the smart nodes 200 will receive a message from the backend server 230 to notify the nodes of candidate CHs.

In S1303, smart nodes 200 within communication range may, in 51305, communicate battery levels among each other, and the smart node 200 with the highest battery level will be known by these smart nodes 200.

In S1307, a smart node 200 may select a CH 201 within its communication range based on a determination of a candidate CH that has the highest battery level in a cluster 210.

The smart node that is selected as CH will, in 51309, announce its election to all its neighboring nodes within communication range, and then, in S1311, these nodes will attempt to join the closest CH node, for example based on signal strength, to form a cluster for the selected CH.

The method in FIGS. 12 and 13 saves energy and reduces communication traffic by reducing the number of messages that are transmitted through the RFID reader 220 to the back-end server 230.

B. Security Policies

For smart nodes 200 to ensure the integrity of the arrived data, as well as authenticate the source of data, the smart nodes store a shared AES 128 bits key. When a node writes the 48 bytes data to its tag, the data is signed with a 16 bytes signature. To obtain the signature, the controller calculates the MD5 128 bits hash value of the 48 data bytes. Then, the obtained hash is encrypted with the AES 128 bits shared key. The result is the signature and is stored on the tag. To verify a newly read tag, the controller computes the hash of the new data (but not the signature), encrypts it with the shared key, and compares the result with the signature. The new data is valid if the result and signature match. Otherwise the new data will be considered as invalid and the smart node's data will be discarded.

An aspect of the present disclosure includes a healthcare monitoring method and system based on an RFID clustering scheme. In order to meet the practical requirements for applying the system in large-scale environments, energy use by the application must be low, and communication quality must be high. In embodiments of the disclosure, the clustering scheme S909 (in FIG. 9) is performed by the backend server 230. The clustering scheme may use an integer programming model having the following objectives:

1. Minimizing the total distance between cluster heads (CHs) and cluster members (CMs).
2. Minimizing the number of clusters.

The first objective, which is to minimize the total distance between all CHs and their respective CMs, is meant to improve positioning accuracy. For each cluster, the CH node is responsible for the positioning information of the cluster members. Minimizing CH-CM distances allows for communication via short-range interfaces, which is more accurate than using long-range interfaces. In addition, shorter distances improve the signal quality and reduce the time delay of transmissions within each cluster.

The second objective is pursued because minimizing the number of clusters reduces signal transmission traffic, lowering the interference between signals. This results in reducing the use of energy and maximizing the lifetime of the network.

Definitions

Let i=1 to n denote the CM number, j=1 to n denote the CH number, Dij denote the distance between CM i and CH j, and F denote the fixed cost per CH. The user's battery level (BL) is defined as in (1). Expressions (2) and (3) define the decision variables, Xij and Yj, which are integer binary variables.

$$BL_j = \begin{cases} 1, & \text{if device } j \text{ has } BL \geq 50\% \\ 0, & \text{otherwise} \end{cases} \quad (1)$$

$$X_{ij} = \begin{cases} 1, & \text{if } CM\ i \text{ is in the cluster of } CH\ j \\ 0, & \text{otherwise} \end{cases} \quad (2)$$

$$Y_j = \begin{cases} 1, & \text{if node } j \text{ is a } CH \\ 0, & \text{otherwise} \end{cases} \quad (3)$$

The complete integer programming model of the network clustering problem is given by (4). The first expression in (4) is the objective function Z, which consists of two terms. The first term is the total distance between CHs and CMs, and the second term is the total number of clusters in the network.

To perform the clustering scheme, the backend server 230 minimizes an objective function Z subject to four sets of constraints. Constraint (I) ensures that every CM has a CH. Constraint II finds the optimal cluster size (CS). Constraint III ensures that all cluster members are within the RFID range of their CH, e.g. not more than two feet away. Finally, Constraint IV ensures that a CH node's battery level has to be at least 50%. The fixed cost of each CH is denoted by F and it is equal to 100.

$$\text{Min } Z = \sum_{i=1}^{n} \sum_{j=1}^{n} (D_{ij} X_{ij}) + F \sum_{j=1}^{n} Y_j \quad (4)$$

Subject to

I. $\sum_{j=1}^{n} X_{ij} = 1, i = 1 \ldots n$

II. $\sum_{i=1}^{n} X_{ij} \leq CS\ Y_j, j = 1 \ldots n$

III. $\sum_{j=1}^{n} D_{ij} X_{ij} \leq 2, i = 1 \ldots n$

IV. $Y_j \leq BL_j, j = 1 \ldots n$

Performance Evaluation

The performance of the disclosed approach was evaluated by three methods. Solutions obtained from the integer programming model are presented below followed by simulation model results. Real experiments are also presented.

A. Solution

The General Algebraic Modeling System (GAMS) is a system for modeling and solving linear programming (LP), nonlinear programming (NLP), and mixed integer programming (MIP) optimization problems. See GAMS Software GmbH (2017). GAMS Specifications, GAMS Website, (gams.com), incorporated herein by reference in its entirety. Since the above model described in expression (4) is a binary integer program, it was solved by the MIP feature of GAMS. GAMS Version 24.3.3 was used, and the problem was considered with two different scenarios.

The first scenario solves the problem by considering the two terms in the objective function that aim to minimize the number of clusters and the total distance between CHs and CMs in order to find the cluster size CS in Constraint II. The second scenario applies sensitivity analysis by fixing the total number of nodes first to n=400 and then to n=500. This is done while changing the fixed cost of each CH, F, and calculating the value of the number of clusters and the total distance as well.

Both scenarios are analyzed under the following environment. The size of the service region is set as 10 by 30 square feet. The value of the objective function is calculated by using GAMS MIP solver, assuming the following different values for the number of nodes n: 400, and 500. In order to achieve 95% confidence interval, each experiment was repeated 10 times using different random input values such as the distances between CHs and CMs and the battery level.

FIGS. 14-17 show the results for scenario 1 (minimizing the total distance and minimizing number of clusters for 400 nodes and 500 nodes). It can be observed from FIG. 14 and FIG. 15 that the total distance between the CHs and the CMs is reduced on average when cluster size is equal 7 (i.e. one cluster head and six cluster members). For example, with 400 nodes, the minimum distance is about 163 feet when cluster size is equal 7, whereas with cluster size equal to 5 the distance is about 168 feet, and is about 167 feet when cluster size is greater than 7. Similar to 500 nodes, the minimum distance is about 230 feet when cluster size is equal 7, whereas with cluster size equal to 5 the distance is about 290 feet, and 270 feet when cluster size is greater than 7. Therefore, the clustering approach is effective in reducing the total distances when cluster size is equal 7, especially for a large-scale system. A higher accuracy of positioning can be achieved, since short-range radio interfaces are more effective than long-range radio interfaces for localization. Shorter distances also reduce the energy consumption and the transmission delay of networks.

Figure 16:
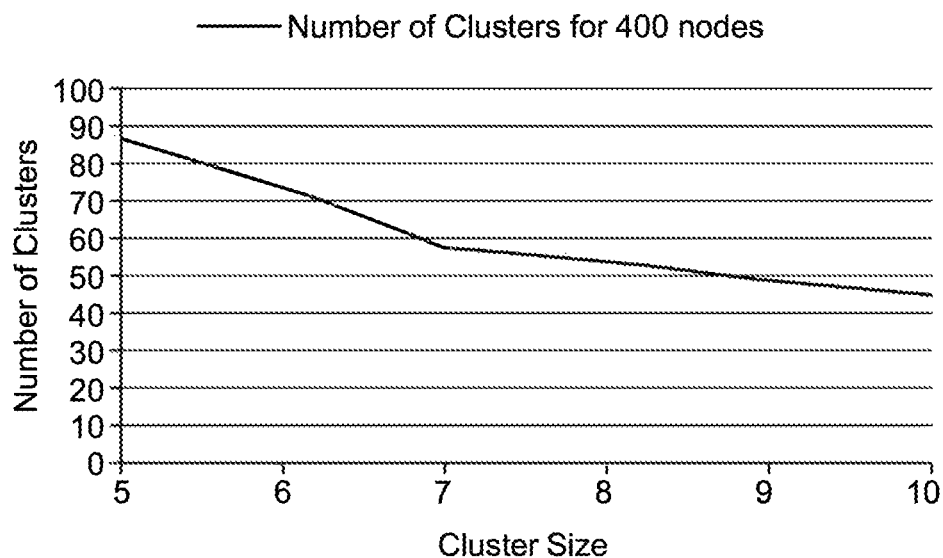
FIG. 16 is a graph illustrating the number of clusters when changing CS for 400 nodes.
Figure 17:
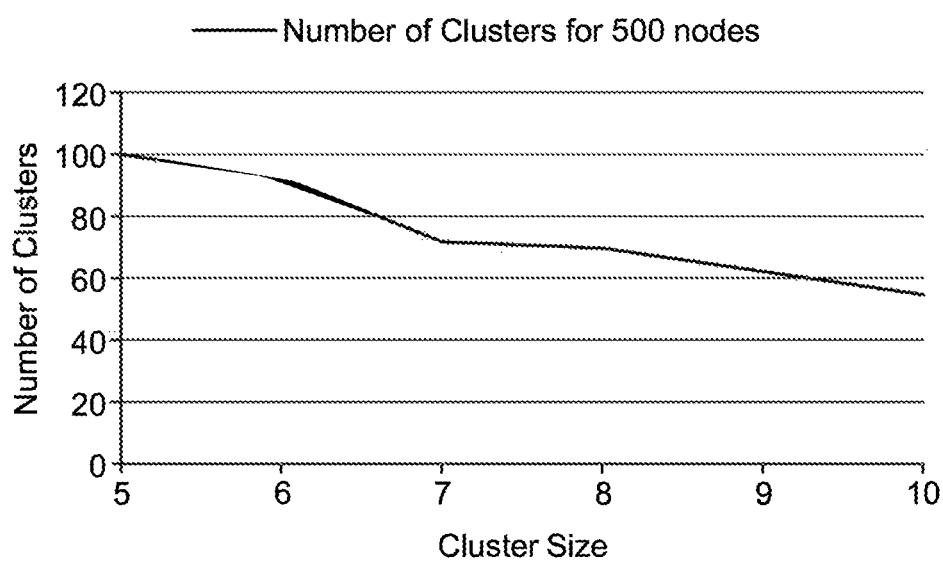
FIG. 17 is a graph illustrating the number of clusters when changing CS for 500 nodes.

FIGS. 16 and 17 show numbers of clusters while cluster size is changing. It can be seen from FIG. 16 and FIG. 17 that the number of clusters is reduced on average when cluster size is increased. However, both terms are of interest in order to achieve the accuracy of positioning and maximize the life time of the network. For instance, with 400 nodes, the minimum distance is about 163 feet when cluster size is equal 7, and with 500 nodes, the minimum distance is about 230 feet when cluster size is equal 7. Therefore, the value of cluster size is equal 7 in order to reduce the total distances and number of clusters as well, especially for a large-scale system. A higher accuracy of positioning can be achieved, since short-range radio interfaces are more effective than long-range radio interfaces for localization. Shorter distances also reduce the energy consumption and the transmission delay of networks. Minimizing the number of clusters reduces signal transmission traffic, and lowers the interference between signals. Thus, minimizing the number of clusters reduces the energy consumption and maximizes the lifetime of the network.

Figure 18:
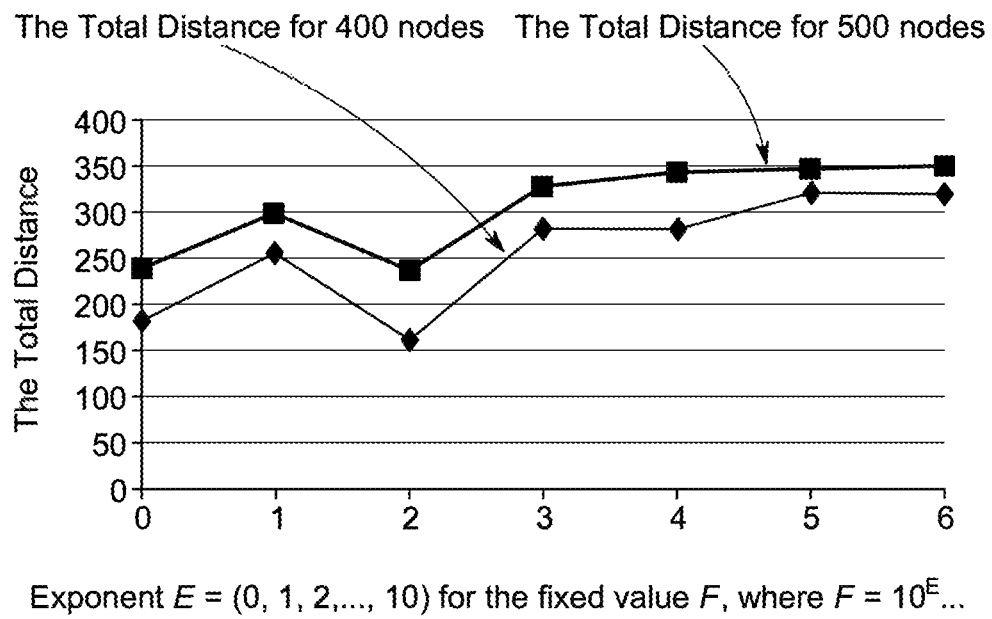
FIG. 18 is a graph illustrating the number of clusters when changing F for 400, 500 nodes.

FIG. 18 demonstrations the total distance of the model when the fixed cost per master F is equal to $10^E$, where E=0, 1, 2 . . . , 10. For 400 nodes, the optimal (minimum) total distance is 160 feet, which is obtained when F is equal to 100 (E=2). For the case of 500 nodes, the optimal total distance is 235 feet, which is also obtained when F is equal to 100. These numbers indicate that the clustering approach is well-suited for large-scale monitoring applications.

Figure 19:
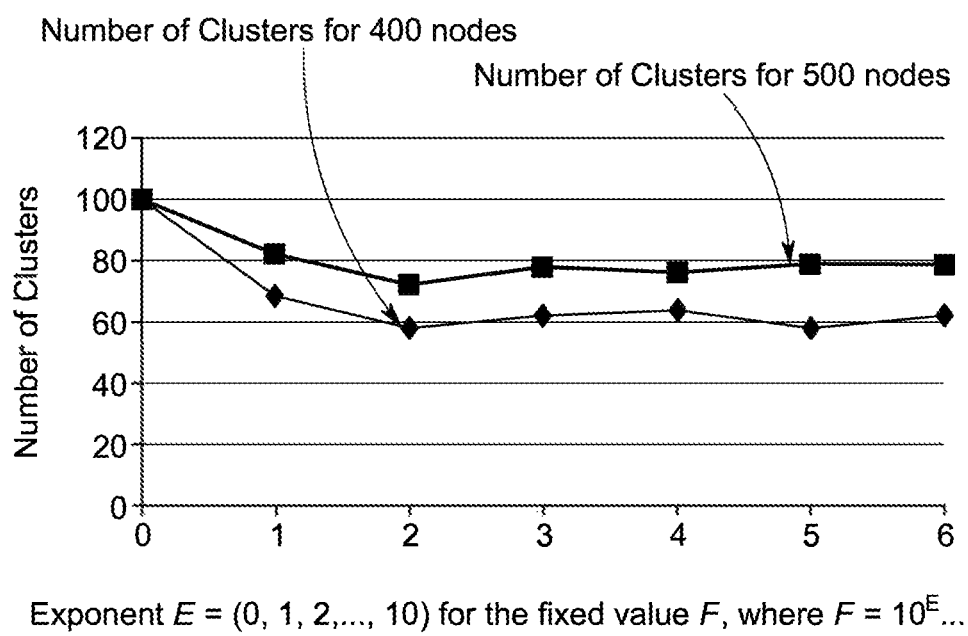
FIG. 19 is a graph illustrating the Total Distance when changing F for 400, 500 nodes.

FIG. 19 illustrates the optimal number of the clusters when the value of fixed cost per master F is equal to $10^E$ where E=0, 1, 2 . . . , 10. For 400 nodes, the optimal (minimum) number of the clusters is 58 clusters, which is obtained when E=2, or F=100. For the case of 500 nodes, the optimal number of clusters is 72 clusters, which is obtained also when F=100. Therefore, the best value of F for both terms to work effectively is 100.

B. Simulation Results

The performance of the clustering approach and the traditional approach (direct approach) were evaluated by using Packet Tracer 7.0 since it supports IoT, RFID, and many other functions and python as programming language in the simulation. Both approaches are implemented with different number of nodes for 10 minutes (600 seconds).

FIG. 20 shows a sample of the collected data at the back-end server 230. It can be observed from FIG. 18 that when the smart node 200 collects the sensed data, it appends it with a timestamp and stores the information in its own tag through RFRR. Subsequently, the transmitted data between smart nodes 200 and RFID readers 220 has three fields, namely, smart node ID which belongs to a specific sensor node, the sensed data, and a timestamp when the data was collected.

The main goal of the clustering scheme is designing and implementing a framework that integrates RFID with wireless sensor systems to gather information efficiently. The main challenge related to that is collecting and protecting real time data and management of it, especially in a health related system that has important and critical data. The RFID nodes will deployed in an open area. Therefore, the attackers can simply access, take control and manage these nodes. Thus, in order to protect health related data from potential attacks Rivest-Shamir-Adleman (RSA) security algorithms may be applied against threats arising from node attacks. FIG. 19 displays a sample of the collected data at the back-end server after implemented (RSA) Algorithm. See Kumar D. Modeling and Representation to Support Design-Analysis Integration. Master Thesis, Department of Civil Engineering, Indian Institute of Technology; 2009, incorporated herein by reference in its entirety.

Figure 22:
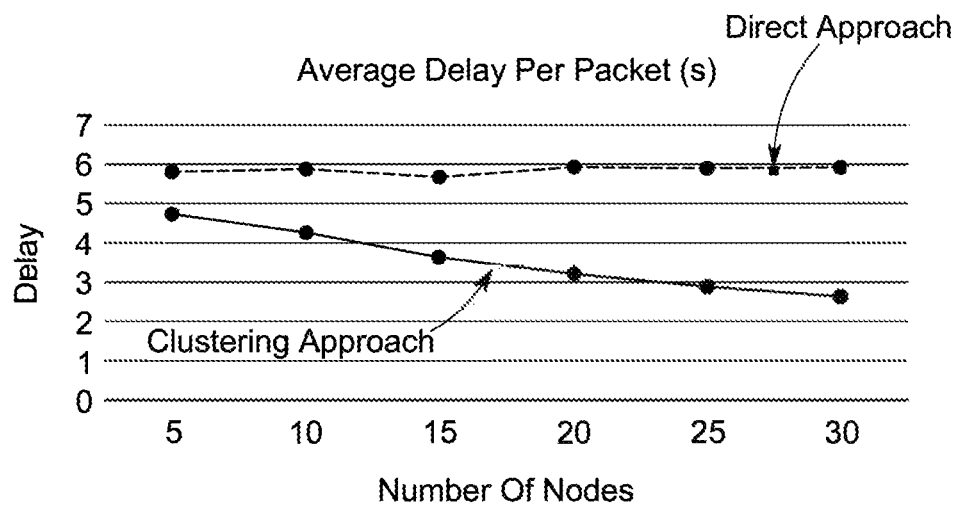
FIG. 22 is a graph illustrating the comparison of the average transmission delay.

FIG. 22 illustrates the results of the average transmission delay per packet of different number of nodes. It can be seen that as the number of nodes increases, the transmission delay per packet of the clustering approach decreases slightly. The explanation of that is because when number of nodes increases in the same region area, the density increases as the number of the cluster heads increases. Therefore, the probability of detecting cluster heads to forward their packets to the RFID reader 220, then to the back-end server 230 increases, which leads to reduced transmission delay. The transmission delay per packet in the direct approach is almost fixed. The reason for this is because the probability of the each node to detect the RFID readers and to forward its packets is the same. In the direct approach, every node has packets which can be transmitted to an RFID reader when each one detects an RFID reader. In the clustering approach, the cluster head 203 has all the packets of the cluster 210 and forwards them to an RFID reader 220 when it detects an RFID reader 220, which significantly reduces the transmission delay per packet.

Figure 23:
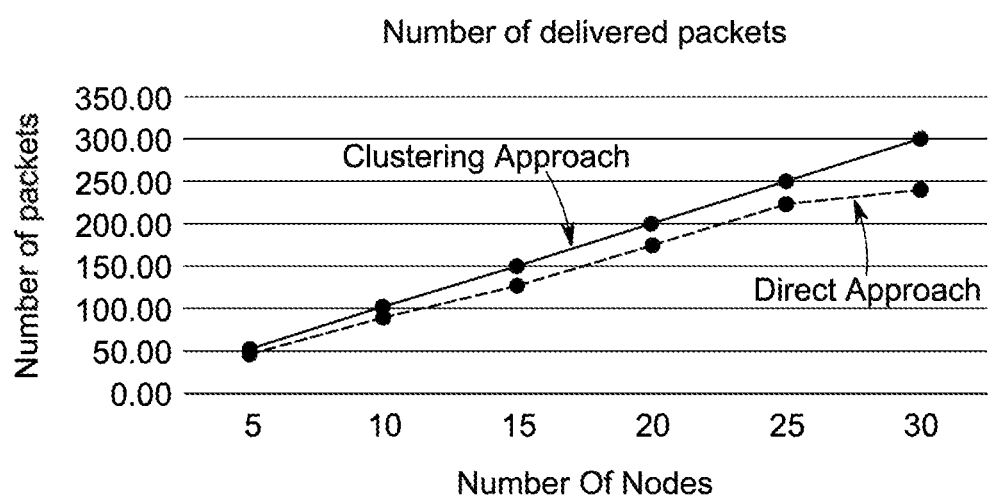
FIG. 23 is a graph illustrating the comparison of number of the delivered packets.

FIG. 23 displays the resulting number of the delivered packets for different number of nodes. In the clustering scheme it can be seen that as the number of nodes increases, the number of delivered packets increases. This is because when the number of nodes are increasing in the same region area, the density also increases which leads to more packets being sent. Therefore, the probability of delivered packets increases. Whereas in the direct approach the probability for each node detecting an RFID reader is the same and smaller than detecting the cluster head which leads to a drop some of packets, because of the channel access congestion. It can be observed from the FIG. 23 that as number of nodes increases in the direct approach, the number of dropped packets increases.

C. Experiment Setup and Results

In this section, the performance of the clustering approach was evaluated and an experiment setup was used for carrying out the experiment. First, the experimental setup and then the experimental results are described.

1. Experiment Setup

A system is set up which is based on the clustering scheme in real experiment scenario. The experimental scenario consists of three smart nodes 200 and one RFID reader 220. The construction of the cluster 210 depends on the choice of the cluster head 203 from nodes in the same range. Each node reads the tag id of all nodes in its communication range. The node which has the highest battery level will be chosen as the cluster head 203 of this cluster 210. Then, each member 201 in the cluster sends their tag information to the cluster head 203. Afterward, the RFID reader 220 receives all packets of nodes from the cluster head 203 instead of reading every tag when they move into the RFID reader range. Finally, the RFID readers 220 send the collected information to the back-end server 230 for data processing and management. It can be observed from FIG. 20 that the RFID reader is attached with external antenna to increase the transmission range of the RFID reader as compared to that of the RFRR. (Indicated by the power enhancements in DB due to adding external antenna).

2. Experiment Results

Figure 24:
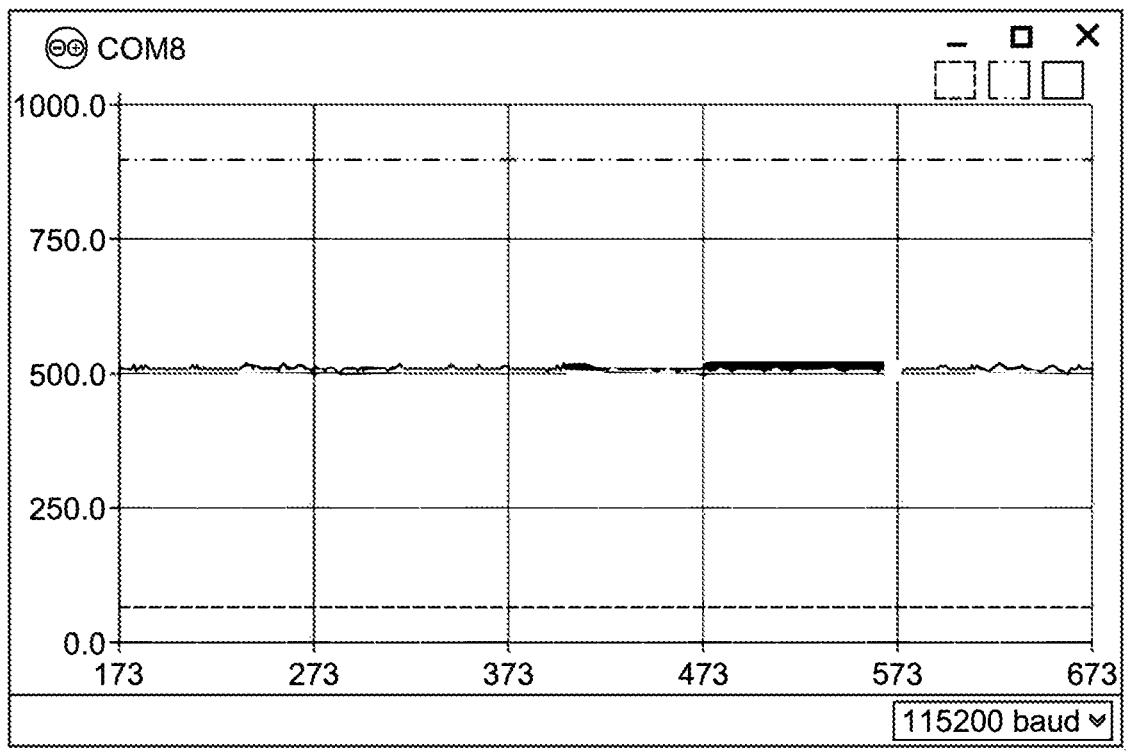
FIG. 24 illustrates a sample of the collected data of the pulse sensor on the serial plotter.
Figure 25:
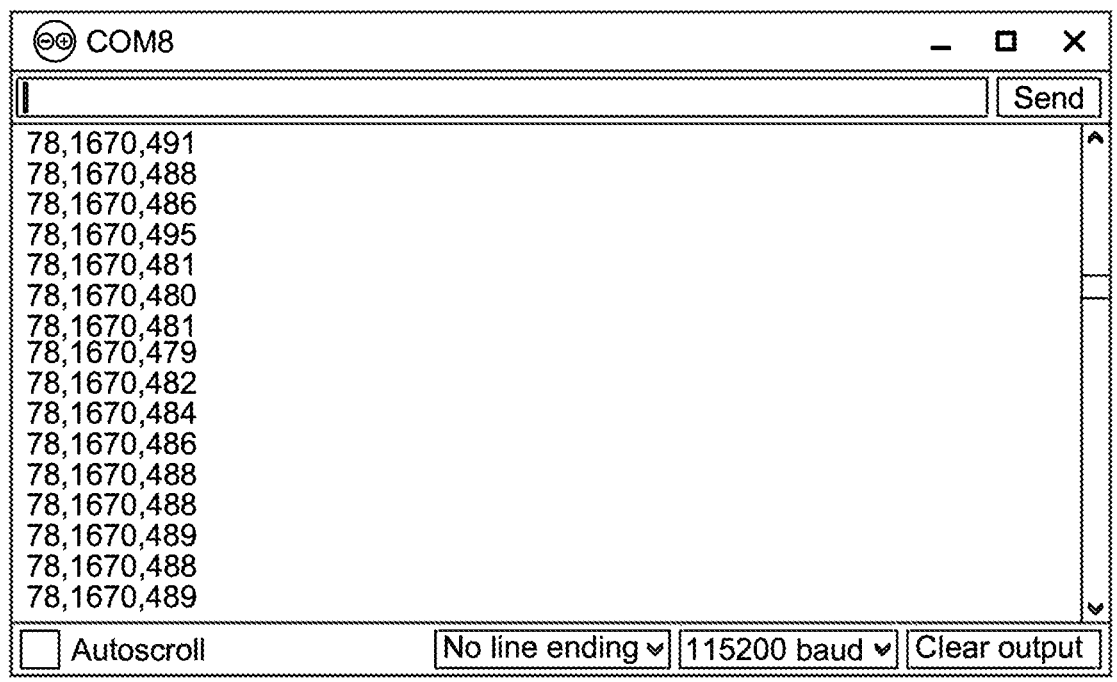
FIG. 25 illustrates a sample of the collected data of the pulse sensor on the serial monitor.

FIG. 24 and FIG. 25 show a sample of the collected data of the pulse sensor that includes the beats per minute, live heart beat and the analog signal on the serial monitor and the serial plotter, respectively. The normal readings of the beats per minute of the pulse sensor should be between 60 and 100. Otherwise, it will be considered as emergency case.

Figure 26:
FIG. 26 illustrates a valid foreign tag one is read and then updated on the serial monitor.

FIG. 26 and FIG. 27 show the result of the experimental scenario which consists of three smart nodes and one RFID reader. Node three which has the highest battery level is chosen as cluster head for this particular cluster and node one and node two are chosen as cluster members. Then, node one and node two send their sensed data to the cluster head which will store this data on its own tag and all information is sent to an RFID reader through the node three, the RFID reader being one that the information reaches first within its range. It can be observed from FIG. 26 and FIG. 27 that a valid foreign tag is one that is read and updated and a valid foreign tag two is one that is read and then updated on the serial monitor, respectively.

FIG. 28 shows captured data packets in an invalid foreign tag four for instance, which was reported by the reader as a result of the authentication process.

The disclosed system and method provides a technique for IoT monitoring applications based on an RFID clustering scheme by integrating RFID with wireless sensor systems to gather information efficiently in smart cities, aiming to monitor and collect data related to health conditions such as the activity levels, emotional state, or physical condition of a large number of people in events such as sporting events, political speeches, concerts, festivals, shopping plazas or malls, airports, train stations, theaters, etc.

The developed system consists of a wearable smart node. The smart node consists of an RFID tag, reduced function of RFID reader and bio pulse sensor. A difference between the disclosed architecture (clustering approach) and the traditional architecture (direct approach) includes that, in the direct approach only the nodes in the range of the RFID readers can send their tag data to the RFID readers. That leads to channel access congestion and therefore the process of collection data will be slow. On the other hand, the disclosed solution (clustering approach) reduces the channel access congestion, thus reducing interference. Also, the disclosed solution reduces the transmission delay, thus collecting the information between nodes in efficient way for a large-scale system that because all information can be sent to an RFID reader through the cluster head that reaches first to its range instead of reading every tag, which significantly makes the process of collection data fast. The developed solution and the experimental results show that the disclosed solution ensures promising results, especially for a large-scale system. Furthermore, the developed solution may be expanded, such as by integrating the node with other sensors to ensure full health care application. In addition, developed solution may lead to good quality of service.

The invention claimed is:

1. A sensor-based monitoring system that collects data to measure health conditions of a plurality of people at an event, the sensor-based monitoring system comprising:
  a computer system;
  a plurality of smart nodes for each of the plurality of people, each smart node including a radio frequency identification (RFID) tag, a wireless sensor network communication device, and at least one body sensor; and
  at least one RFID reader device,
  wherein the computer system includes circuitry configured to
    determine candidate cluster heads as smart nodes with above average battery level,
  wherein each of the plurality of smart nodes are configured to
    determine a subset of the candidate cluster heads that are within communication range,
    retrieve a battery level of the determined subset of cluster heads,
    select a cluster head having the highest battery level,
  wherein the selected cluster head is configured to
    send a message to announce selection as the selected cluster head,
    receive messages, from the plurality of smart nodes that are within communication range, requesting to join a cluster,
    read sensor data of the body sensor in each joined smart sensor as collective sensor data for the cluster, and
    send the collective sensor data to the computer system via the at least one RFID reader,
  wherein the circuitry of the computer system is further configured to
    measure the health conditions of the plurality of people at the event based on the sent collective sensor data.

2. The sensor-based monitoring system of claim 1, wherein
  each of the plurality of smart nodes are wearable smart nodes that include a Reduced Function RFID reader (RFRR), at least one medical sensor including a body temperature sensor, pulse sensor and muscle activity sensor as the at least one body sensor, a RFID tag and a microcontroller, and
  wherein the RFID reader device has a greater transmission range than the RFRR.

3. The sensor-based monitoring system of claim 2, wherein memory of the RFID tag is divided into data slots and a slot for authentication, each data slot includes an ID of the respect smart node, a sequence number, and data,
  wherein, when new sensor data arrives, the microcontroller of the smart node determines whether a slot contains data for a previous ID, updates the data if the sequence number is less than a new sequence number of the new data.

4. The sensor-based monitoring system of claim 1, wherein the RFRR of one of the plurality of smart nodes reads sensor data of other smart nodes' tags and stores the read sensor data into its own RFID tag.

5. The sensor-based monitoring system of claim 1, wherein
  the circuitry forms clusters of the smart nodes that
  minimize the total distance between cluster heads and other smart nodes in order to improve positioning accuracy for the smart nodes, and
  minimize the number of the clusters in order to reduce the signal transmission traffic.

6. The sensor-based monitoring system of claim 4, wherein
  the circuitry forms clusters of the smart nodes that minimizes the total distance between cluster heads and other smart nodes, and minimizes the number of the clusters is in accordance with the function $$\text{Min } Z = \sum_{i=1}^{n} \sum_{j=1}^{n} (D_{ij} X_{ij}) + F \sum_{j=1}^{n} Y_j$$

where Dij denotes the distance between cluster member CM i and cluster head CH j, F denotes the fixed cost per cluster head CH, Xij denotes whether CMi is in the cluster of CH j, and Yj denotes whether node j is a CH.

7. The sensor-based monitoring system of claim 6, wherein the function Z is minimized subject to a constraint that every CM has a CH.

8. The sensor-based monitoring system of claim 6, wherein the function Z is minimized subject to a constraint that the number of cluster members is minimum.

9. The sensor-based monitoring system of claim 6, wherein the function Z is minimized subject to a constraint that all cluster members are within an RFID range of their CH.

10. The sensor-based monitoring system of claim 1, wherein
two level security is obtained by,
when a smart node writes the sensor data to its RFID tag from the one or more sensors of the smart node, the sensor data is signed with a signature, which is a hash value, and
the obtained hash is encrypted with a shared key.

11. The sensor-based monitoring system of claim 1, wherein the at least one RFID reader device is further configured to receive the collective sensor data from the cluster heads selected for each cluster.

12. A method for a sensor-based monitoring system that collects data to measure health condition of a plurality of people at an event, the sensor-based monitoring system includes a computer system, a plurality of smart nodes for the plurality of people, and at least one RFID reader device, each of the plurality of smart nodes including a radio frequency identification (RFID) tag, a wireless sensor network communication device, and at least one body sensor, the at least one body sensor including at least one of a body temperature sensor, a pulse sensor and a muscle activity sensor, the computer system includes processing circuitry, the method comprising:
determining, by the circuitry, candidate cluster heads as smart nodes with above-average battery level,
each of the plurality of smart nodes:
determining a subset of the candidate cluster heads that are within communication range,
retrieving battery level of the determined subset of cluster heads, and
selecting a cluster head having the highest battery level, the selected cluster head:
sending a message to announce selection as the selected cluster head,
receiving messages, from the plurality of smart nodes that are within communication range, requesting to join a cluster,
reading sensor data of the body sensor in each joined smart sensor as collective sensor data for the cluster, and
sending the collective sensor data to the computer system via the at least one RFID reader,
measuring, by the circuitry, the health conditions of the plurality of people at the event based on the sent collective sensor data.

13. The method of claim 12, further comprising reading, by a smart node, sensor data of other smart nodes' tags and storing the read sensor data into the smart nodes' own RFID tag.

14. The method of claim 12, further comprising:
forming of clusters of the smart nodes by
minimizing the total distance between cluster heads and other smart nodes in order to improve positioning accuracy for the smart nodes, and
minimizing the number of the clusters in order to reduce the signal transmission traffic.

15. The method of claim 14, wherein
the forming clusters of the smart nodes minimizes the total distance between cluster heads and other smart nodes, and minimizes the number of the clusters is in accordance with the function $$\text{Min } Z = \sum_{i=1}^{n} \sum_{j=1}^{n} (D_{ij} X_{ij}) + F \sum_{j=1}^{n} Y_j$$

where Dij denotes the distance between cluster member CM i and cluster head CH j, F denotes the fixed cost per cluster head CH, Xij denotes whether CMi is in the cluster of CH j, and Yj denotes whether node j is a CH.

16. The method of claim 15, wherein the function Z is minimized subject to a constraint that every CM has a CH.

17. The method of claim 15, wherein the function Z is minimized subject to a constraint that the number of cluster members is minimum.

18. The method of claim 15, wherein the function Z is minimized subject to a constraint that all cluster members are within an RFID range of their CH.

19. The method of claim 12, wherein
two level security is obtained by,
when a smart node writes the sensor data to its RFID tag from the one or more sensors of the smart node, generating a signature with a hash value to sign the sensor data, and
encrypting the obtained hash with a shared key.

20. The method of claim 12, wherein memory of an RFID tag is divided into data slots and a slot for authentication, each data slot includes an ID of the respect smart node, a sequence number, and data,
the method further comprising, when new sensor data arrives, determining, by the microcontroller of the smart node, whether a slot contains data for a previous ID, and
updating the data if the sequence number is less than a new sequence number of the new data.

* * * * *